United States Patent
Flynn et al.

(10) Patent No.: US 11,619,730 B2
(45) Date of Patent: Apr. 4, 2023

(54) METHOD AND SYSTEM FOR CODED EXCITATION IMAGING BY IMPULSE RESPONSE ESTIMATION AND RETROSPECTIVE ACQUISITION

(71) Applicant: VERASONICS, INC., Kirkland, WA (US)

(72) Inventors: John A. Flynn, Seattle, WA (US); Lauren S. Pflugrath, Seattle, WA (US)

(73) Assignee: Verasonics, Inc., Kirkland, WA (US)

( * ) Notice: Subject to any disclaimer, the term of this patent is extended or adjusted under 35 U.S.C. 154(b) by 998 days.

(21) Appl. No.: 15/563,387

(22) PCT Filed: Mar. 30, 2016

(86) PCT No.: PCT/US2016/025050
§ 371 (c)(1),
(2) Date: Sep. 29, 2017

(87) PCT Pub. No.: WO2016/161009
PCT Pub. Date: Oct. 6, 2016

(65) Prior Publication Data
US 2018/0088220 A1    Mar. 29, 2018

Related U.S. Application Data

(60) Provisional application No. 62/141,749, filed on Apr. 1, 2015.

(51) Int. Cl.
*A61B 8/14* (2006.01)
*G01S 7/52* (2006.01)
(Continued)

(52) U.S. Cl.
CPC .......... *G01S 7/52093* (2013.01); *A61B 8/06* (2013.01); *A61B 8/14* (2013.01); *A61B 8/4483* (2013.01);
(Continued)

(58) Field of Classification Search
CPC ............ G01S 7/52093; G01S 15/8979; G01S 7/52077; G01S 15/8959; G01S 7/5202;
(Continued)

(56) References Cited

U.S. PATENT DOCUMENTS 5,938,611 A * 8/1999 Muzilla ............... G01S 7/52047
600/455
6,213,947 B1 * 4/2001 Phillips ............... G01S 7/52038
600/443
(Continued)

FOREIGN PATENT DOCUMENTS

CN     103901416 A   *  7/2014
CN     104398271 A   *  3/2015    ......... G01S 15/8979
(Continued)

OTHER PUBLICATIONS

English translation of DE-10303797-A1 (Google Patents, 2021).*
(Continued)

*Primary Examiner* — Mark D Remaly
(74) *Attorney, Agent, or Firm* — Seed Intellectual Property Law Group LLP

(57) ABSTRACT

A method that includes transmitting coded waveforms simultaneously on multiple elements for several frames, constructing a first multi-input, single output (MISO) system from the codes to model transmit-receive paths, solving system and RF data observation by linear model theory, giving an IR set for the medium, and applying the estimates to a secondary MISO system, constructed by analogy to the first, but with pulses convenient for beamforming in the form of a focused set of single-cycle pulses for ideal focused reconstruction.

7 Claims, 14 Drawing Sheets

Ultrasound Imaging System

(51) Int. Cl.
*A61B 8/06* (2006.01)
*B06B 1/02* (2006.01)
*G01S 15/89* (2006.01)
*G10K 11/34* (2006.01)
*A61B 8/00* (2006.01)
*A61B 8/08* (2006.01)

(52) U.S. Cl.
CPC .............. *A61B 8/485* (2013.01); *A61B 8/488* (2013.01); *A61B 8/5207* (2013.01); *A61B 8/5276* (2013.01); *B06B 1/0215* (2013.01); *G01S 7/5202* (2013.01); *G01S 7/52077* (2013.01); *G01S 15/8927* (2013.01); *G01S 15/8959* (2013.01); *G01S 15/8979* (2013.01); *G01S 15/8997* (2013.01); *G10K 11/346* (2013.01); *B06B 2201/76* (2013.01)

(58) Field of Classification Search
CPC .............. G01S 15/8997; G01S 15/8927; G01S 7/52047; G10K 11/346; A61B 8/14; A61B 8/4483; A61B 8/485; A61B 8/488; A61B 8/5207; A61B 8/5276; A61B 8/06; B06B 1/0215; B06B 2201/76

See application file for complete search history.

(56) References Cited

U.S. PATENT DOCUMENTS

| | | | |
|---|---|---|---|
| 6,695,778 B2* | 2/2004 | Golland | G01S 7/5205 600/443 |
| 6,796,944 B2 | 9/2004 | Hall | |
| 7,887,487 B2 | 2/2011 | Hao et al. | |
| 9,117,439 B2* | 8/2015 | Bercoff | G01S 7/52049 |
| 2001/0044278 A1 | 11/2001 | Chiao et al. | |
| 2004/0136608 A1 | 7/2004 | Rosenfeld | |
| 2004/0220465 A1* | 11/2004 | Cafarella | A61B 5/0507 600/407 |
| 2005/0171429 A1 | 8/2005 | Mathew et al. | |
| 2007/0161904 A1* | 7/2007 | Urbano | A61B 8/4438 600/459 |
| 2008/0249408 A1 | 10/2008 | Palmeri et al. | |
| 2010/0185093 A1 | 7/2010 | Hamilton | |
| 2012/0163691 A1* | 6/2012 | Walker | A61B 8/00 382/131 |
| 2013/0144165 A1 | 6/2013 | Ebbini et al. | |
| 2014/0018668 A1 | 1/2014 | Zheng et al. | |
| 2014/0371594 A1 | 12/2014 | Flynn et al. | |
| 2015/0080725 A1 | 3/2015 | Wegner | |
| 2016/0101436 A1* | 4/2016 | Stice | G01S 7/5202 600/459 |

FOREIGN PATENT DOCUMENTS

| | | | | |
|---|---|---|---|---|
| DE | 10303797 A1 * | 5/2004 | | A61B 8/13 |
| WO | 2015/009960 A1 | 1/2015 | | |
| WO | 2015/013196 A1 | 1/2015 | | |

OTHER PUBLICATIONS

Chiao et al. "Coded Excitation for Diagnostic Ultrasound: A System Developer's Perspective." IEEE Trans Ultrasonics, Ferroelectrics, and Frequency Control: 52(2), pp. 160-170. 2005.*

International Search Report and Written Opinion of the International Searching Authority, dated Sep. 2, 2016, for the International Application No. PCT/US2016/025050, 21 pages.

Flynn, J.A., "Computation and Architectures for Array Receivers in Large Delay-Doppler Spreading," Ph.D. dissertation, Department of Electrical Engineering, University of Washington, 2004, 198 pages.

Flynn, J.A., et al., "Arbitrary Waveforms Using a Tri-State Transmit Pulser," *Ultrasonics Symposium (IUS), 2013 IEEE International*, Prague, Czech Republic, Jul. 2013, pp. 41-44.

Flynn, J.A.; Ritcey, J.A., "Turbo array receiver for underwater telemetry," *Signals, Systems and Computers, 2004. Conference Record of the Thirty-Eighth Asilomar Conference on*, vol. 2, Nov. 7-10, 2004, pp. 1421-1425.

Gran, F., et al., "Identification of Pulse Echo Impulse Responses for Multi Source Transmission," *Conference Record of the Thirty-Eighth Asilomar Conference on Signals, Systems and Computers* 1-2:168-172, IEEE, 2004.

* cited by examiner

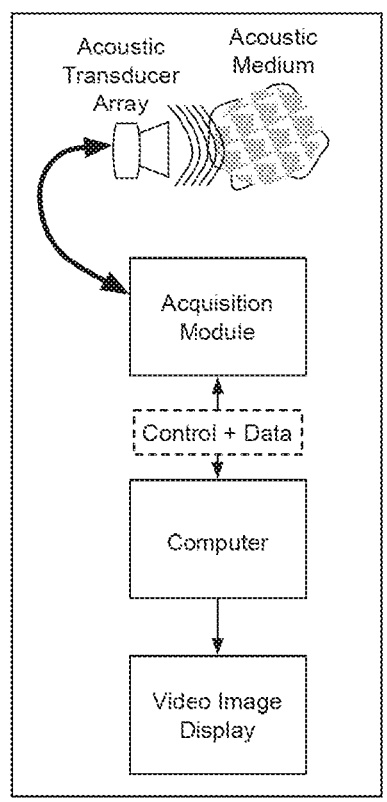
Figure 1 Ultrasound Imaging System

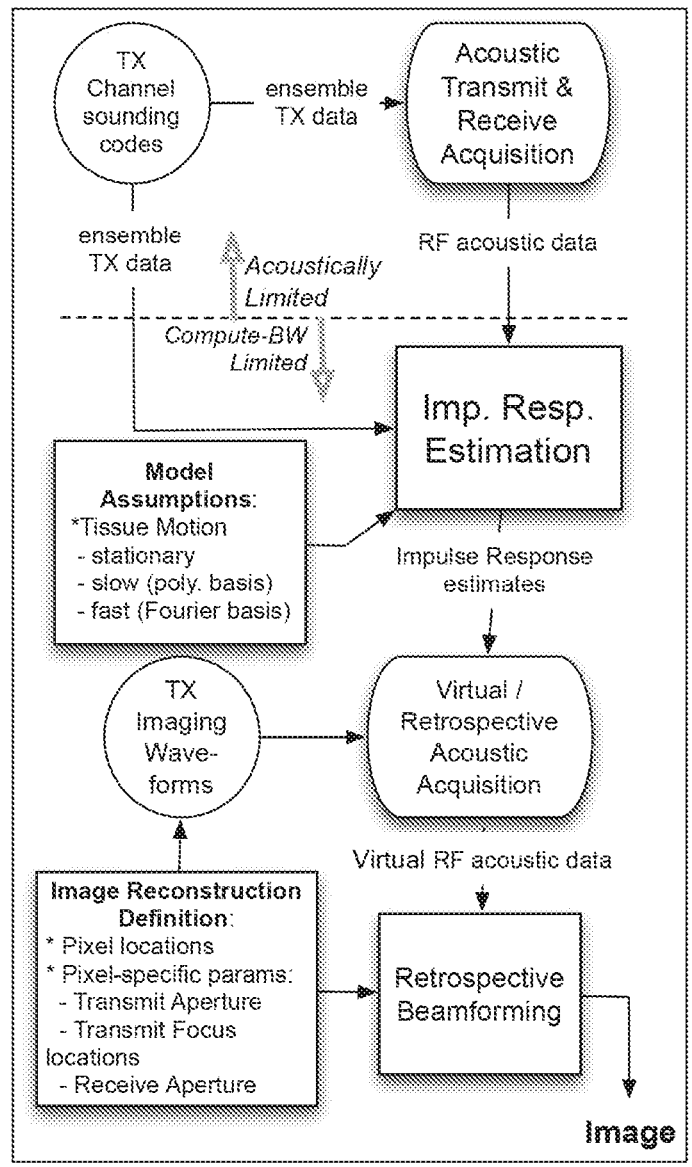
Figure 2 - Coded Excitation Reconstruction Process.

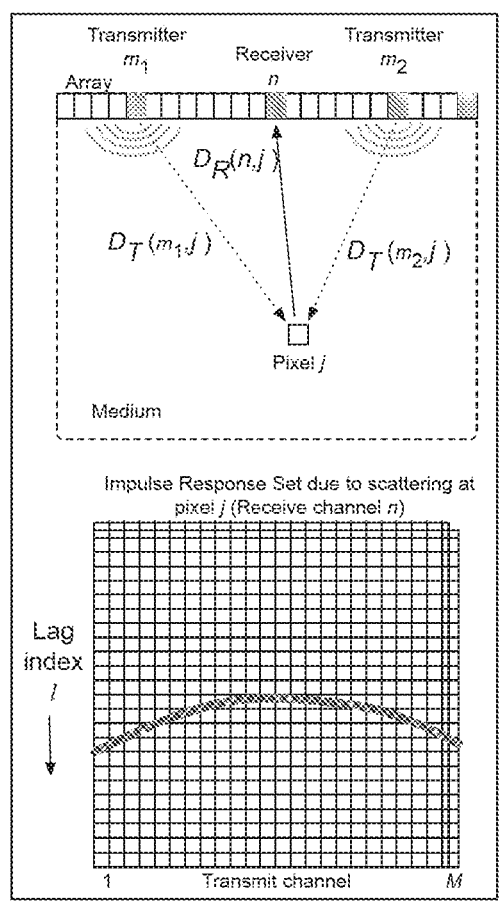
Figure 3 Schematic relation between reconstructed pixel (top panel) and impulse response lags (bottom panel).

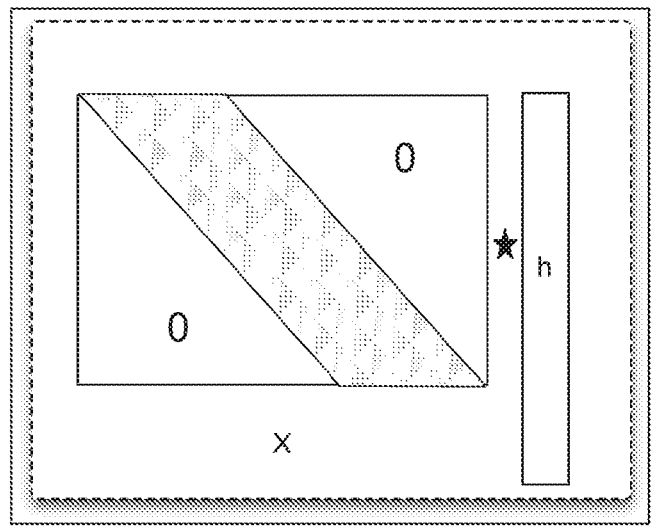
Figure 4 - Schematic form and sparsity structure of Toeplitz matrix operator for fully-convolved impulse response.
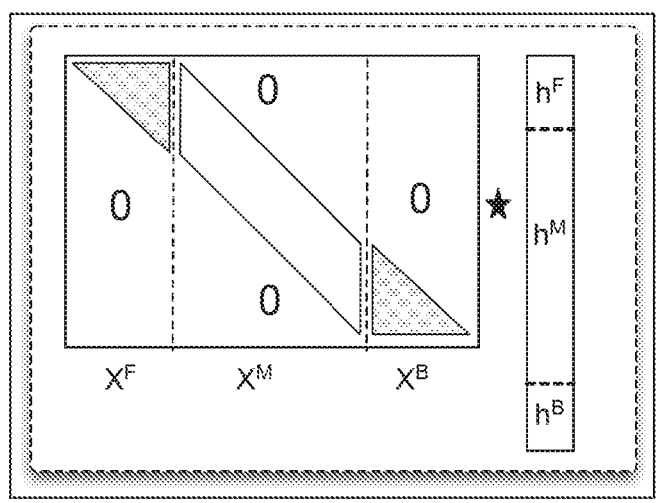
Figure 5 - Schematic form of sparsity structure and partitioning of matrix operator for convolution in the mixed-effects model.

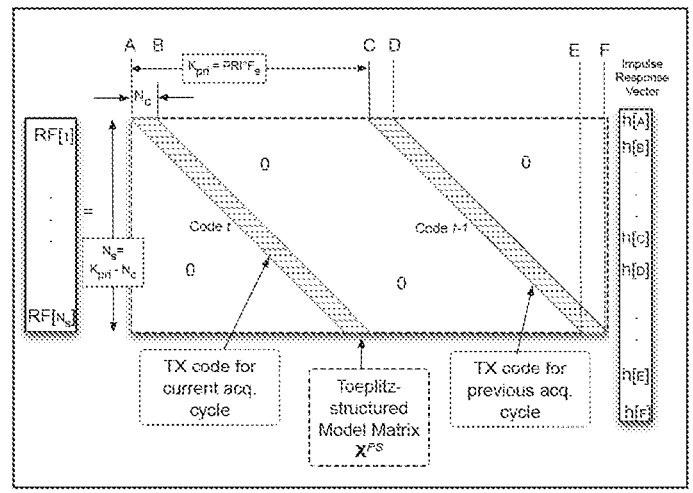
Figure 6 - Schematic of convolution operator sparsity structure for pulse-stacking (high-Doppler) model for a single acquisition.
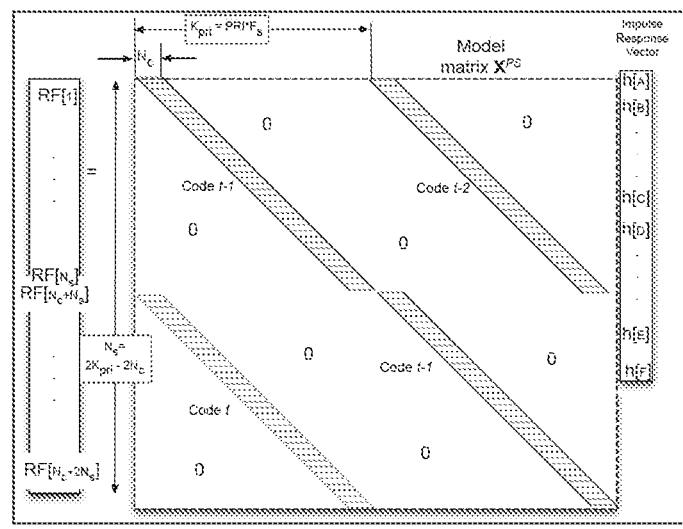
Figure 7 - Schematic of sparsity structure for high-Doppler model (two acquistion intervals).

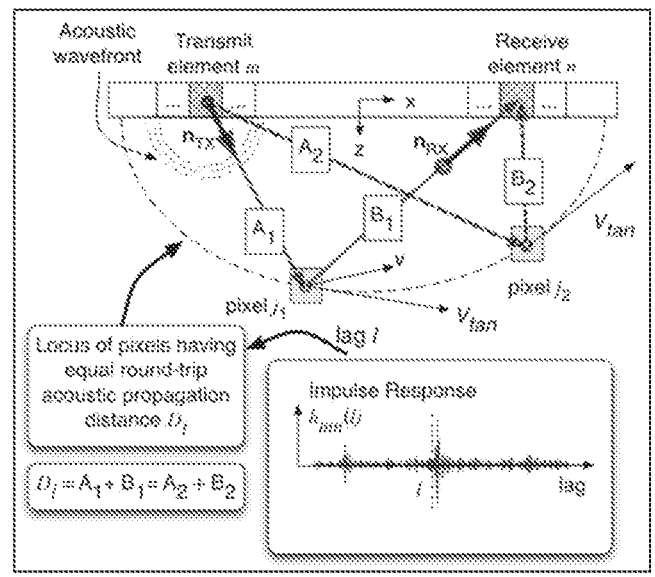
Figure 8 - Geometry and definitions for motion effects on observed Doppler in impulse response.
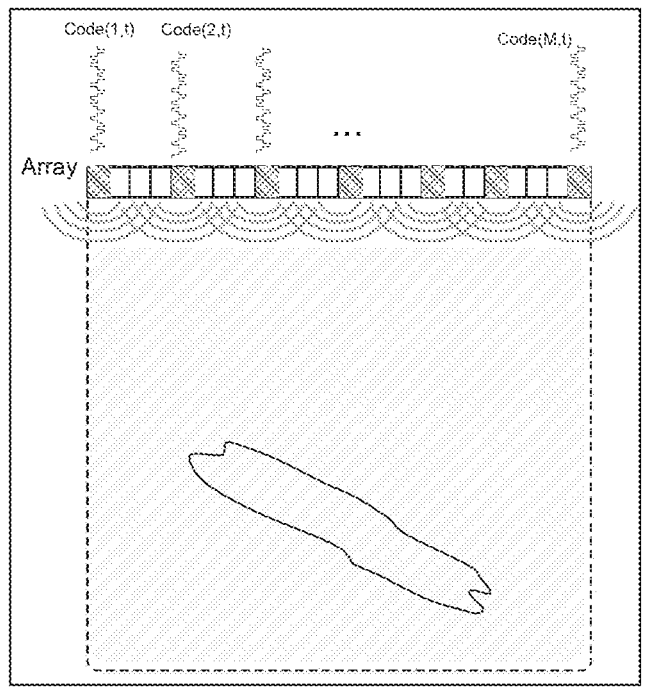
Figure 9 - Schematic of a sparse transmit element configuration.

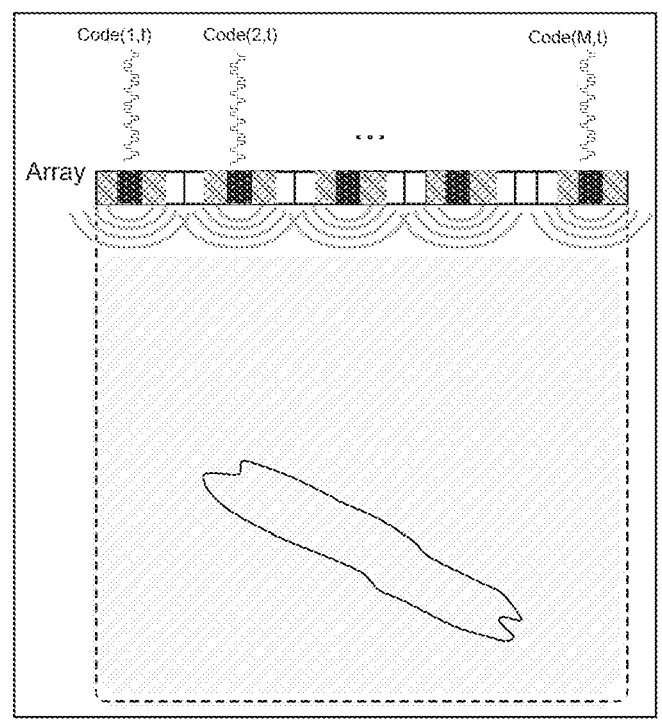
Figure 10 - Schematic of sparse transmit aperture with extended elements.

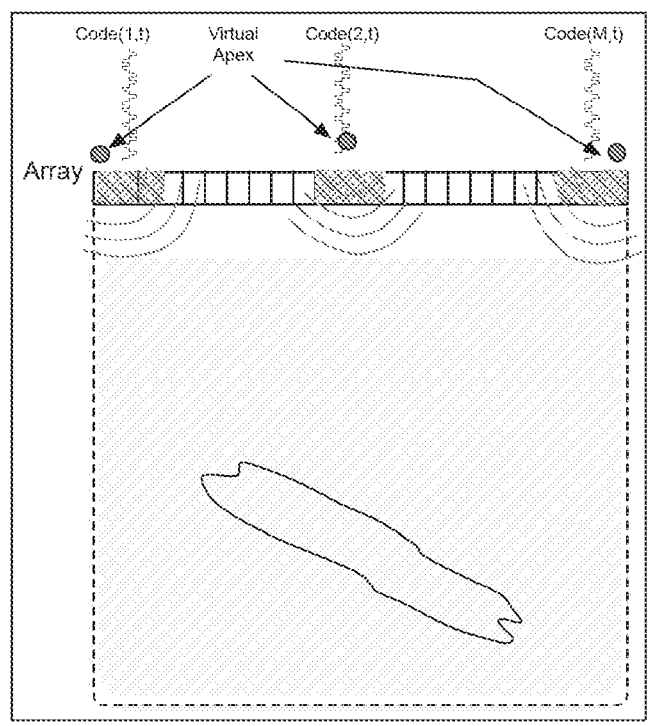
Figure 11 - Schematic of sparse transmit aperture with virtual apex source locations

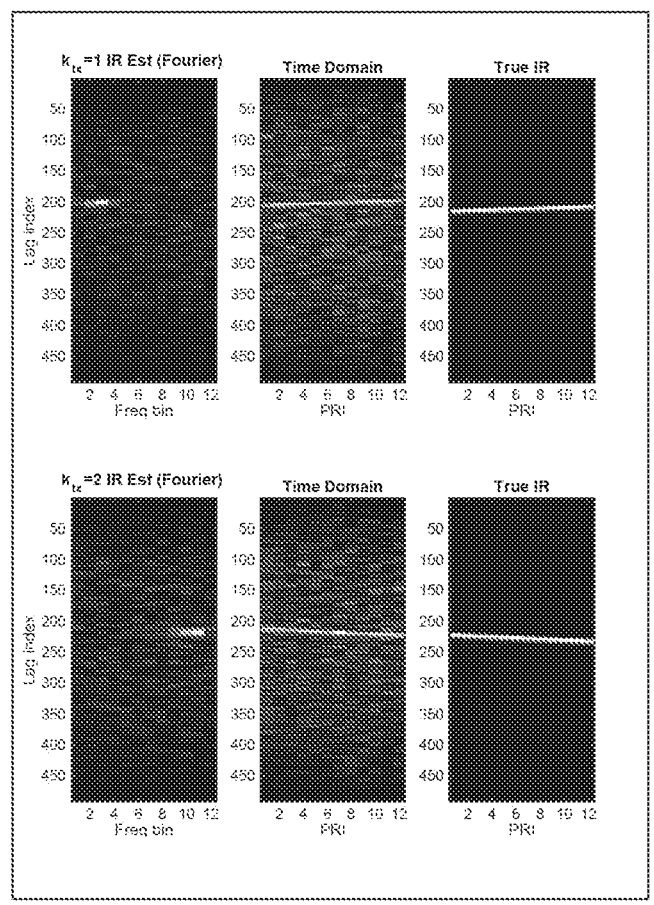
Figure 12 - Simulation example of coded excitation impulse response estimation of moving target (low-flow STR algorithm)

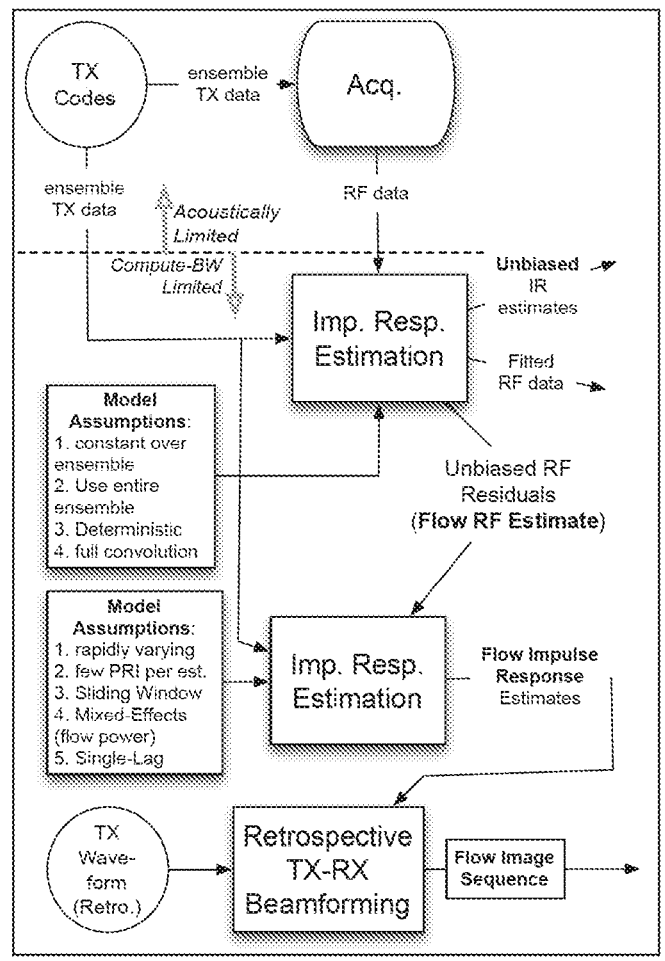
Figure 13 - Architecture for CER algorithm for stationary tissue rejection and blood flow imaging

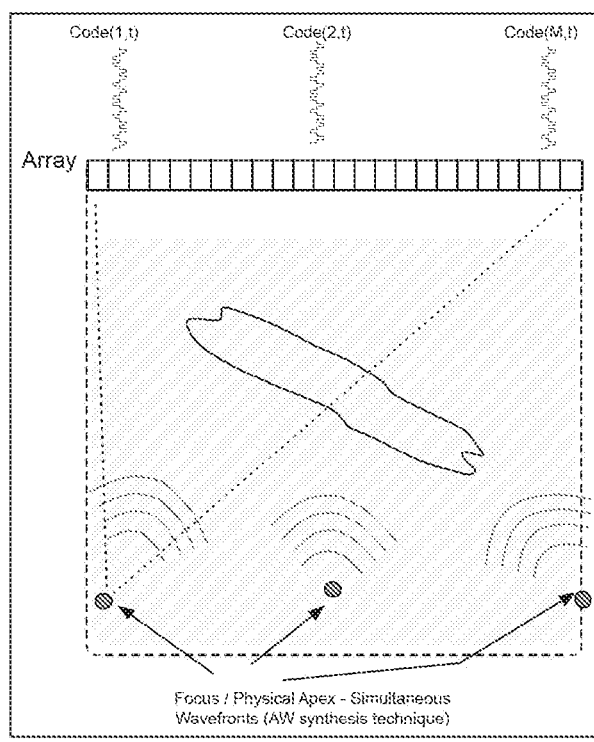
Figure 14 - Virtual source locations for simultaneous wavefront synthesis.

```
1. Compute Doppler-indexed
impulse response set
H(m,n,lag,fDopp) per Section
III.C 3. Define:
f_Dopp = GetDoppBin(V,m,n,j) per
bistatic range-rate equation:
f_Dopp = [n_TX - n_Rx] * V *(f/c)

4. Define vector velocity grid
over
[v_xMin < v_x < v_xMax] and [v_zMin < v_z <
v_zMax]

5. Compute pixels in image:

For each pixel j,
   For each velocity V=[Vx,Vz]
in grid
      For each Receive element n,
```

Figure 15 - Algorithm steps for CER-based vector motion imaging

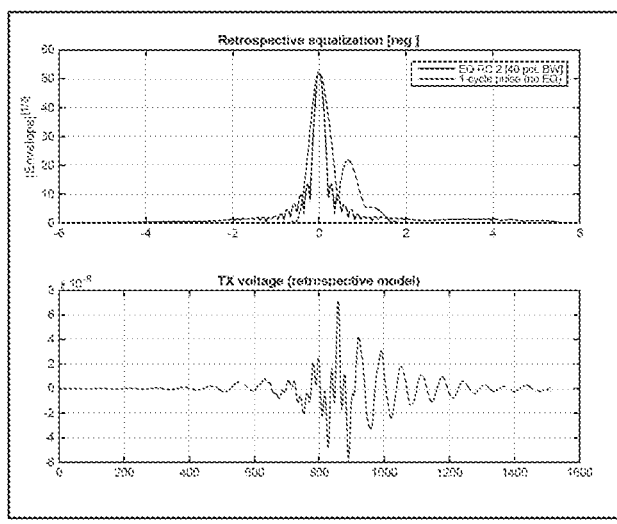

Figure 16 - Transducer compensation example application of arbitrary waveform synthesis during retrospective transmission

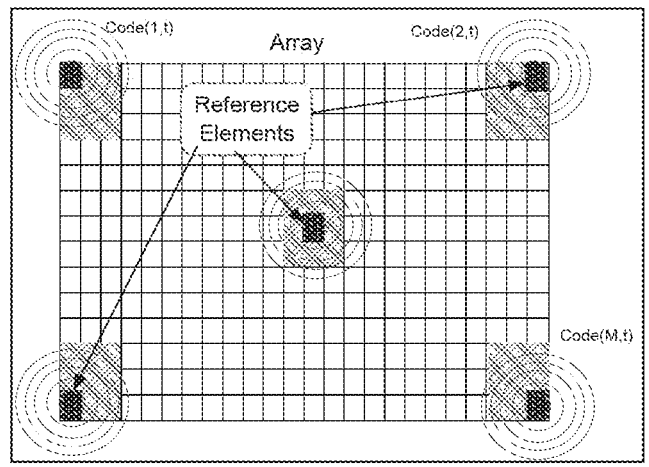
Figure 17 - Sparse transmit aperture example configuration for CER 3D imaging with 2D array
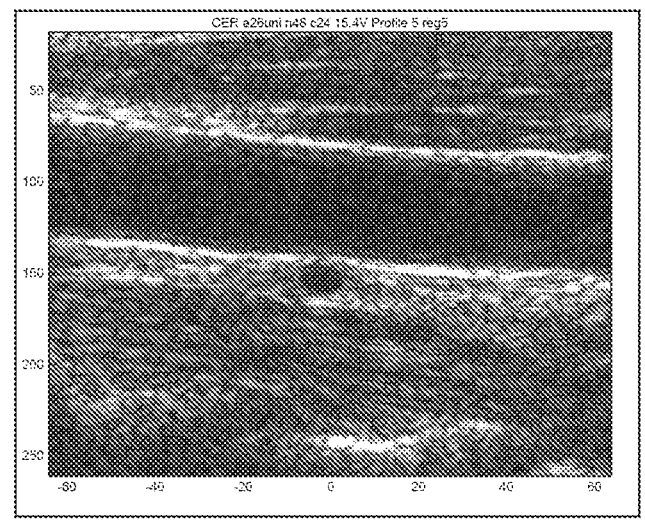
Figure 18 - CER carotid imaging example in vivo using Philips L7-4 transducer.

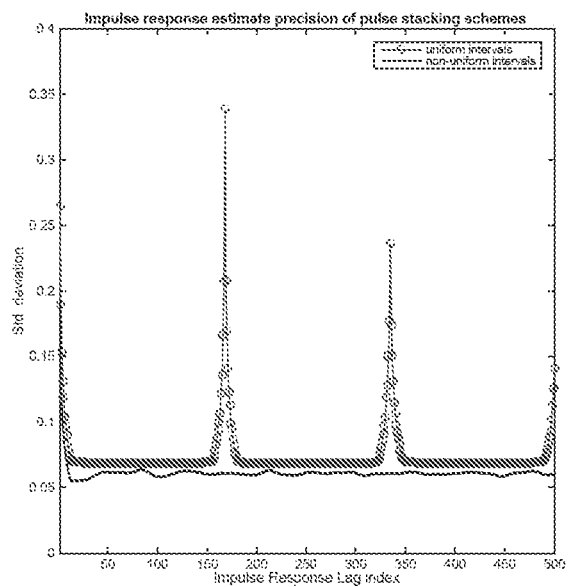
Figure 19 - Estimate precision comparison of hypothetical uniform and non-uniform pulse stacking models.
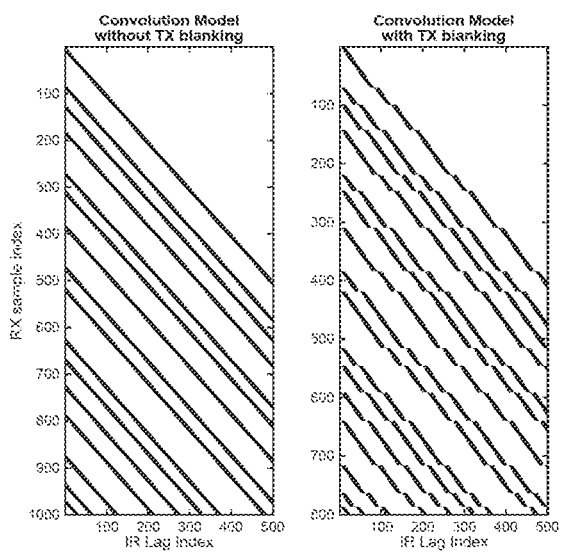
Figure 20 - Illustration of non-uniform pulse stacking approach and its misalignment of blanking intervals.

METHOD AND SYSTEM FOR CODED EXCITATION IMAGING BY IMPULSE RESPONSE ESTIMATION AND RETROSPECTIVE ACQUISITION

CROSS REFERENCE TO RELATED APPLICATION

This application claims the benefit under 35 U.S.C. § 119(e) to U.S. Provisional Application No. 62/141,749 filed on Apr. 1, 2015, which application is incorporated by reference herein in its entirety.

BACKGROUND

Technical Field

The present disclosure pertains to methods for encoding arbitrary waveforms into a sequence suitable for control of a tri-state RF ultrasonic transmitter, under various fidelity criteria, and to a related system.

Description of the Related Art

Coded pulse excitation provides the opportunity to design waveforms with large time-bandwidth products, which is a means to improve signal penetration while maintaining resolution in coherent imaging. However, with the distributed scattering typical of ultrasonic imaging, clutter induced by pulse compression side lobes, and cross-channel correlation cause reduced contrast resolution.

BRIEF SUMMARY

The present disclosure is directed to a system and process that implements a two-step method for coded excitation imaging that first estimates the medium's impulse response (IR), then by retrospective transmission through the IR set, synthesizes virtual wavefronts for beamforming.

In step one, coded waveforms are transmitted simultaneously on multiple elements for several frames. A multi-input, single output (MISO) system is constructed from the codes to model transmit-receive paths. The system and RF data observation are solved by linear model theory, giving an IR set for the medium. In step 2, the estimates are subsequently applied to a secondary MISO system, constructed by analogy to the first, but with pulses convenient for beamforming, e.g., a focused set of single-cycle pulses for ideal focused reconstruction. Thus, the probing sequence can be optimally designed for IR characterization under acoustic time budget, while the retrospective acquisitions are synthesized outside of acoustic time.

The implementation of the method demonstrates that under typical imaging system constraints and assumptions, this approach provides a framework to achieve optimal unbiased estimation of beamformed pixels. Using a research ultrasound platform, the method I demonstrated on a phantom and in-vivo.

In accordance with one aspect of the present disclosure, a method is provided that includes transmitting coded waveforms simultaneously on multiple elements for several frames; constructing a first multi-input, single output (MISO) system from the codes to model transmit-receive paths; solving system and RF data observation by linear model theory, giving an impulse response (IR) set for the medium; and applying the estimates to a secondary MISO system, constructed by analogy to the first, but with pulses configured for beamforming in the form of a focused set of single-cycle pulses for focused reconstruction.

In accordance with another aspect of the present disclosure, a method is provided that includes ultrasonic imaging by coded excitation reconstruction (CER), comprising using coded excitation transmission emitted from multiple transducer elements or apertures simultaneously over a time sequence of multiple acquisition events, processing subsequently received RF ultrasound data on transducer elements in a manner that estimates a set of multi-input-single-output (MISO) impulse response acoustic models, one for each transmit-receive transducer channel pair; and subsequently employing a secondary step comprising virtual acquisition of virtual RF data through excitation of the MISO models repeatedly as a proxy for the imaged media present, and subsequently beamforming or image reconstruction using the virtual RF data to produce imagery.

In accordance with a further aspect of the present disclosure, a method is provided that includes ultrasonic imaging by coded excitation reconstruction (CER), further including emitting acoustic signals into a medium simultaneously from multiple transducer elements using coded excitation transmission over a time sequence; receiving echo signals at the multiple transducer elements in response to the emitting; processing the received echo signals in a manner that estimates a set of multi-input-single-output (MISO) impulse response acoustic models, one for each transmit-receive pair at each transducer element; acquiring virtual data through excitation of the MISO model repeatedly as a proxy for the imaged media present, and image reconstruction using the virtual data to produce a visual image on a display device.

In accordance with still yet another aspect of the present disclosure, a method for ultrasonic tissue motion imaging is disclosed that includes emitting acoustic signals into a medium simultaneously from multiple transducer elements using coded excitation transmission over a time sequence; receiving echo signals at the multiple transducer elements in response to the emitting; processing the received echo signals, which comprises estimating a set of multi-input, single-output (MISO) impulse response acoustic models, one for each transmit-receive pair at each transducer element and that retains corresponding estimation fitting error residuals conforming to data used, so that stationary tissue signals are rejected in the fitted residuals, while blood flow or motion-induced Doppler signals of interest are retained therein; and processing the residuals data to produce blood flow or moving tissue imagery.

In accordance with yet a further aspect of the present disclosure, a system is provided that includes means for transmitting coded waveforms simultaneously on multiple elements for several frames; means for constructing a first multi-input, single output (MISO) system from the codes to model transmit-receive paths; means for solving system and RF data observation by linear model theory, giving an IR set for the medium; and means for applying the estimates to a secondary MISO system, constructed by analogy to the first, but with pulses configured for beamforming in the form of a focused set of single-cycle pulses for focused reconstruction.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein:

FIG. 1 is a first embodiment of an ultrasound imaging system formed in accordance with the present disclosure;

FIG. 2 is an illustration of the Coded Excitation Reconstruction Architecture formed in accordance with the present disclosure;

FIG. 3 is a schematic relation between reconstructed pixel (top panel) and impulse response lags (bottom panel) in accordance with the present disclosure;

FIG. 4 is a schematic form and sparsity structure of a Toeplitz matrix operator for fully-convolved impulse response in accordance with the present disclosure;

FIG. 5 is a schematic form of a sparsity structure and partitioning of a matrix operator for convolution in the mixed-effects model of the present disclosure;

FIG. 6 is a schematic of a convolution operator sparsity structure for pulse-stacking (high-Doppler) model for a single acquisition; and FIG. 7 is a schematic of a sparsity structure for a high-Doppler model (two acquisition intervals) in accordance with the present disclosure;

FIG. 8 is illustrates a geometry and definitions for motion effects on observed Doppler in an impulse response;

FIG. 9 is a schematic of a sparse transmit element configuration;

FIG. 10 is a schematic of a sparse transmit aperture with extended elements;

FIG. 11 is a schematic of a sparse transmit aperture with virtual apex source locations;

FIG. 12 are screen shots of a simulation example of coded excitation impulse response estimation of a moving target (low-flow STR algorithm);

FIG. 13 is an illustration of architecture for CER algorithm for stationary tissue rejection and blood flow imaging;

FIG. 14 illustrates the virtual source locations for simultaneous wavefront synthesis;

FIG. 15 illustrates the steps of the steps for CER-based vector motion imaging;

FIG. 16 illustrates a transducer compensation example application of arbitrary waveform synthesis during retrospective transmission;

FIG. 17 illustrates a sparse transmit aperture example configuration for CER 3-D imaging with 2-D array;

FIG. 18 is a CER carotid imaging example in vivo using a Philips L7-4 transducer;

FIG. 19 is an estimate precision comparison of hypothetical uniform and non-uniform pulse stacking models; and FIG. 20 is an illustration of non-uniform pulse stacking approach and its misalignment of blanking intervals.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures or components or both associated with ultrasound imaging as discussed herein have not been shown or described in order to avoid unnecessarily obscuring descriptions of the embodiments.

Unless the context requires otherwise, throughout the specification and claims that follow, the word "comprise" and variations thereof, such as "comprises" and "comprising" are to be construed in an open inclusive sense, that is, as "including, but not limited to." The foregoing applies equally to the words "including" and "having."

Reference throughout this description to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

I. Introduction

As discussed above, coded pulse excitation provides a means to improve signal penetration while maintaining resolution in coherent imaging. However, with the distributed scattering typical of ultrasonic imaging, clutter induced by matched-filter pulse compression sidelobes reduces contrast resolution. The present disclosure addresses this issue with a two-step method that first estimates the medium's impulse response (IR), then by retrospective transmission through the IR set, synthesizes virtual wavefronts for beamforming.

In step one, coded waveforms are transmitted simultaneously on multiple elements for several frames. A multi-input, single output (MISO) system is constructed from the codes to model transmit-receive paths. The system and RF data observation are solved by linear model theory, giving an IR set for the medium. In step two, the estimates are applied to a secondary MISO system, constructed by analogy to the first, but with pulses convenient for beamforming, e.g., a focused set of single-cycle pulses for ideal focused reconstruction. Thus, the probing sequence can be optimally designed for IR characterization under acoustic time budget, while the retrospective acquisitions are synthesized outside of acoustic time. Under typical imaging system constraints and assumptions, this approach provides a framework to achieve optimal unbiased estimation of beamformed pixels.

Linear model theory shows how precision of the IR estimates can be controlled at desired central lags, at the expense of noise at distal lags. Also the IR estimation model will be poorly conditioned, and pseudoinverse solutions induce IR estimate bias. However, by interpreting the beamforming operation on the secondary MISO system as a function of the IR estimates, the theory of estimable functions provides conditions under which the resulting pixels nonetheless are unbiased. Thus inherent pixel bias is characterized for designs, apart from a specific medium.

The disclosed two-step approach has the following advantages: (1) it decouples the sidelobe design problem from the signal penetration problem; (2) allows retrospective transmission of arbitrary waveforms without the need for coding techniques accommodating limited transmit voltage levels (e.g., [20]; (3) allows a flexible and gradual tradeoff between framerate, mainlobe resolution, and contrast resolution, and sensitivity.

Computation:

Three implementation approaches with distinct tradeoffs between computation resources and application requirements are described.

Previous Work:

An Evaluation of BPSK-based channel impulse response estimation and retrospective transmission applied to ocean acoustic telemetry was conducted to predict modulation scheme performance in specific realizations of the observed acoustic environment. This method is generalized to the case of multiple simultaneous and independent transmit channels.

II. Description

The disclosed method and process is meaningful in the context of an ultrasound data transceiver acquisition and imaging system, whose purpose is to generate imagery from an ultrasonic medium. A schematic of one implementation of the architecture of such a system is shown in FIG. 1. Refer to Table 1 for definition of key variables and terminology.

The two-step process is used in order to facilitate its motivation in the sequel as an optimal estimation of pixels of the synthetic aperture ideal focus (SAIF) beamformer; however, the process can be combined into a one-step filtering of the received RF data for implementation purposes. The two steps are (1) estimate an impulse response characterization of the acoustic media present, and (2) retrospectively transmit through the resulting media model a set of virtual wavefronts and execute the SAIF imaging beamformer. An overview of the process implementing the methodology of the present disclosure is shown in FIG. 2.

The first step of the algorithm estimates the set of impulse responses between every transmit channel and every receive channel. The acquisition process for this step transmits a set of coded sequences simultaneously on all of the array transmit elements. This is repeated for several pulse repetition intervals, forming an ensemble, with a unique coded sequence being used for each pulse repetition interval. The codes are comprised of binary symbols, employed in a phase-shift keying (BPSK)—modulation of a one-cycle waveform appropriate for the transducer, with the symbol rate choses as the transducer nominal center frequency.

Note that the term "transmit channel", which indexes a dimension of the set of impulse response vectors according to transmit code, can include the concept of a transmit subarray. A subarray is energized with a single common pulser sequence (i.e., transmit code). To be useful, this generalization requires a beamformer, in step two, that is designed to exploit the subarray geometry.

In the second step, the media characterization defined by the impulse response set is employed to simulate virtual transmission and reception of an imaging sequence. The resulting retrospective acquisition is then processed by the appropriate beamforming algorithm. In our examples, the transmissions are implemented as Kronecker deltas shifted by fractional delay filters to achieve focus at the pixel of interest when convolved with the impulse response estimates. The retrospective acquisition and beamforming process is repeated for all pixels in the imaging region or field-of-view.

Glossary

TABLE 1

Glossary of key terms

| Symbol | Meaning |
|---|---|
| $F_C$ | Transmit center RF frequency |
| k | PRI |
| l | impulse response lag (delay) index |
| m | Transmit channel |
| n | Receive channel |
| t | Fast-time RF sample |

TABLE 1-continued

Glossary of key terms

| Symbol | Meaning |
|---|---|
| $N_C$ | Transmitted Code Length |
| r | RF acquisition measurement |
| h | system-acoustic medium impulse response |
| X | transmit signal convolution model |
| cov( ) | Covariance |
| E( ) | statistical expectation |
| BPSK | binary phase-shift keying |
| DAC | digital-to-analog converter |
| DF | dynamic focus |
| DFT | discrete Fourier transform |
| FET | field-effect transistor |
| FIR | finite impulse response (filter or model) |
| IR | impulse response |
| MISO | multi-input, single output |
| PPM | pulse-position modulation |
| PRF | pulse repetition frequency |
| PRI | pulse repetition interval |
| PW | plane-wave |
| RF | radio frequency |
| SAIF | Synthetic aperture ideal focus |
| SEPIC | Single-ended primary inductor converter |
| STR | Stationary tissue rejection |

A. Code Structure and Generation Method

The code transmitted on an array element during a transmit event are generated as a Bernoulli sequence of equiprobable symbols of value in {+1,−1}. We employ this as an expedient way to develop many long, linearly independent code realizations that in practice yield Toeplitz-structured convolution model matrices of rank high enough to facilitate impulse response estimation. Once generated, the realized codes are treated as deterministic because they are known. The code symbols are realizations from a pseudorandom number generator and are i.i.d. across transmit element, transmit cycle (fast time), and PRF (slow time), so that we can argue heuristically that space-time-frequency diversity is achieved with high probability. We take this to imply that a well-conditioned convolution model matrix results (developed in the sequel), given a sufficient number of pulses intervals in the ensemble.

Binary Code Transmission

Each code symbol in a symbol sequence modulates a prototype pulse shape that is, in the simplest case, a single cycle square wave with a period commensurate with the transducer center frequency. Other prototype pulse shapes apply by obvious extension. In a typical imaging example for a 128-element linear array, each burst contains 48 cycles, and therefore 48 binary symbols for each transmit channel. the code symbol values For example, the code symbol values may be in the set {+1,−1}, while the prototype pulse is realized in the transmitter hardware operating at V volts by values [+V,0,−V] in the case of a tri-state pulser circuitry, or by more voltage levels in multi-level transmitters or in the case of a linear transmit amplifiers driven by a digital-to-analog converter (DAC). When the code values are limited to the set {+1,−1}, this linear modulation is known in the communications literature as BPSK signaling.

Linearly modulated codes with more than two levels function ably with the disclosed methods by simply generalizing the values in the resulting model matrix to the modulating symbol values.

Pulse Position Modulation (PPM) codes can be likewise built into the model by selecting different time shifts of a prototype pulse, within upsampled symbol periods, for non-zeros elements defined in the model matrix.

B. Signal Model and Definitions

Throughout this development discrete-time indices are employed. We assume that the modulation, transmitter, medium, and receiver are linear and shift-invariant, and the received signal is corrupted by additive, zero-mean, white noise samples of equal variance. The shift-invariant assumption implies neglect of media motion during the ensemble time (this will be restriction relaxed in the sequel). Then, subject to appropriate bandlimiting, the deterministic part of the signal $r_{mnk}$ received on channel n at discrete time sample t due to signal $x_{mk}(t)$ transmitted on channel m at the k-th PRI, is $$E[r_{mnk}(t)] = h_{mn}(t) * x_{mk}(t) \tag{1.1}$$

where the * operator denotes convolution and E[ ] denotes statistical expectation. Then omitting the time index, the following discrete-time combined impulse response description holds for transmit channel m and receive channel n:

$$h_{mn}(t) = w(t) * p_m^{TX}(t) * p_n^{RX}(t) * h_{mn}^A(t), \tag{1.2}$$

where the achieved transmitter pulse w(t) has shape of time duration $P = 1/F_c$, the transmit and receive directional impulse responses of the array element are respectively $p_m^{TX}(t)$ and $p_n^{TX}(t)$, and the acoustic media impulse response between transmit element m and receive element n is $h^A_{mn}$. For purposes of this paper, the individual components in (1.2) need not be distinctly resolved, and the entire convolution is combined into the aggregate $h_{mn}(t)$ for a given (m,n) pair.

So that the convolution model $h_{mn}$ maps the code symbol sequence $s_{mk}(t)$ specified at the symbol rate to the receiver data sampled at a multiple thereof, we use an interpolation kernel to define the transmitted signal as the zero-fill-interpolated code symbol sequence $$x_{mk}(R_{US}t) = \begin{cases} s_{mk}(t), t = 1, \square, N_C \\ 0 \text{ otherwise} \end{cases} \tag{1.3}$$

This effectively produces interpolated impulse response estimates in the convolution model defined in the sequel. Alternatively, some extensions to the algorithm may require a low-pass interpolation kernel that replicates code values into neighboring interpolated samples (rather than zero filling), or modulates the original code sample to a quadrature by the quadrature interpolation kernel [1, i, −1, −i].

Throughout the presentation we have the modulating symbol rate equal to $F_C$, and the oversample rate of $R_{us}=4$.

Basic Model (Deterministic Scattering)

After the interpolation models have been defined as above, we now have in matrix-vector form the expectation of measurements from the single-transmit channel convolution model (1.1) as $$E(r_{mnk}) = X_{mk} h_{mn} \tag{1.4}$$

where $$r_{mnk} = [r_{mnk}(0) \ldots r_{mnk}(T-1)]^T, \tag{1.5}$$

$$h_{mn} = [h_{mn}(0) \ldots h_{mn}(L-1)]^T, \tag{1.6}$$

and where $$X_{mk} = \begin{bmatrix} x_{mk}(L_x-1) & \ldots & x_{mk}(0) & 0 & \ldots & 0 \\ 0 & & & & \ddots & \vdots \\ \vdots & \ddots & & & \ddots & 0 \\ 0 & \ldots & 0 & x_{mk}(L_x-1) & \ldots & x_{mk}(0) \end{bmatrix} \tag{1.7}$$

has Toeplitz structure, and $X_{mk}$ is dimensioned [Tx(T+$L_x$−1)], with $L_x = R_{US} N_C$. Note that the $N_b$ samples in the received data $r_n$ have been excised, without loss of validity of (1.1) or (1.4), to account for receiver blanking during the transmission time, or to further restrict processing to data at a suitably deep region of interest. This excision implies that corresponding rows of Toeplitz-structured convolution matrix $X_m$ are likewise deleted, as well as the identically zero leading columns of $X_m$, so that corresponding leading elements of vector $h_{mn}$ are not modeled. With simultaneous transmission of code sequences on M multiple channels, the total expected signal at receiver channel n for the collection of K PRIs in the ensemble is $$E(r_n) = Xh \tag{1.8}$$

where the system model for simultaneous transmissions, and joint MISO impulse response h, are respectively $$X = \begin{bmatrix} X_{11} & , \ldots, & X_{1M} \\ \vdots & & \vdots \\ X_{K1} & , \ldots, & X_{KM} \end{bmatrix} \tag{1.9}$$

and $$h = \begin{bmatrix} h_1 \\ \vdots \\ h_M \end{bmatrix} \tag{1.10}$$

with $$\text{cov}(r_n, r_l) = \begin{cases} I\sigma_v^2, n = l \\ O \text{ otherwise} \end{cases} \tag{1.11}$$

C. Impulse Response Estimation

To solve for the collection of impulse responses associated with the j-th receive channel, theory of linear statistical models [8] distinguishes two cases for our stated assumptions: the (full-rank) Gauss-Markov model, and the Gauss-Markov model not of full rank.

In the full-rank case, KT>ML is necessary but not sufficient). The assertion of this condition depends on the number of transmit channels and PRIs in the ensemble, and the specific codes used and their length. The well know least-squares solution results from best linear unbiased estimation criteria, so that the residual sum-of-squares (RSS)

$$\text{RSS} = \|r_n - Xh_n\|^2 \tag{1.12}$$

is minimized over $h_n$, leading to the normal equations $$X'Xh = X'r \tag{1.13}$$

with solution in terms of the Moore-Penrose pseudoinverse $$\hat{h} = X^+ r \tag{1.14}$$

where $$X^+ = (X'X)^{-1} X' \tag{1.15}$$

In the not-of-full rank case, a non-unique solution is produced, leading to the alternate form of the pseudoinverse and a biased estimate of h:

$$X^+ = X(X'X)^{-1} \quad (1.16)$$

While the pseudoinverse will give unique solution h in both cases, in practice we choose to regularize the not-of-full rank case by a simple form of the Tikhonov regularization method by augmenting the normal equations with a term to penalize energy in the estimate h. This leads to the augmented measurement and system model $$r^{Aug} = \begin{bmatrix} X \\ I\sigma_{reg} \end{bmatrix} h \triangleq X_A h \quad (1.17)$$

The solution to the estimation problem in (1.12) is the set of impulse responses $$h_{mn} = [h_{mn}(0), \ldots, h_{mn}(L-1)]^T, \quad (1.18)$$

representing the path between the m-th transmit element and the n-th receive element. Note that in this basic formulation, the estimation procedure and model X are identical for all n receive elements; only the measurement data (and possibly the regularization coefficients) differ among different receive channels n. Therefore, the impulse response estimation computation and data storage are parallelizable by receive channel.

D. Retrospective Transmission and Imaging

The impulse response set (1.18) function as a model acoustically characterizing the structure and state of the physical tissue present during the coded excitation transmission and reception. The IR set H consequently enables retrospective transmission, reception, and subsequent image formation in the second phase of the algorithm.

Because the retrospective acquisitions are executed on a model of the acoustic media present and not on the actual physical tissue represented by the model, they are not subject to acoustic propagation time limitations on framerate. Furthermore, the estimation variance (discussed in Section II.F) achievable in Step 1 is predictably reduced by increasing the length of the coded waveforms and the number of PRIs in the ensemble. This enables the design tradeoff between SNR, clutter, and frame rate to be decided for the estimation step of the algorithm. These considerations thus permit synthetic aperture ideal focus transmission and reconstruction in the retrospective step of the algorithm, while maintaining high effective framerate and high SNR.

Here we give an example of retrospective acquisition and imaging which implements conventional synthetic aperture ideal focus (SAIF) beamforming in a retrospective manner by operating on the estimated impulse response functions to achieve virtual acquisition data; note however, the principle applies to a broad class of general imaging techniques, including though not limited to planewave (PW) imaging and dynamic focus (DF) imaging. The following description develops a pixel-specific retrospective reconstruction notation that sums weighted dot products of the impulse response estimate set. Other mathematically equivalent formulations, such as an FIR filtering description, are essentially identical to the presented description; however, the description below permits a simple, textbook noise performance analysis using standard techniques from Linear Model theory. The retrospective acquisition and imaging for the j-th lexicographically-ordered image pixel F(j) can be represented respectively through the sparse arrays A and b operating on the estimated impulse responses H, as $$F(j) = B(j)[1'_N \otimes A(j)]\hat{H} \text{ or} \quad (1.19)$$

$$F(j) = \sum_n b(j,n) A(j) \hat{H}_n \quad (1.20)$$

where $$\hat{H} = [\hat{H}_1; \square; \hat{H}_N], \quad (1.21)$$

the matrix A(j) contains retrospective transmit channel waveforms $\{a_{mj}(t)\}$, each of length $L_a$ including delays necessary for transmit focusing at the j-th pixel scattering location. Note the impulse response variable is capitalized here to indicate an explicit slow time index in a generalized model described late in (1.51). Vector b(j,n), is the n-th row of matrix B(j), and contains the interpolation weighting to execute receive beamforming delays for partial reconstruction of the j-th pixel on data from receive channel n. A(j) is of a block form, with a single block row, so that $$A(j) = [A_1(j) \ldots A_M(j)] \quad (1.22)$$

where each element block A(j) is a convolution operator of the retrospective transmit waveforms for each transmit channel.

$$A_m(j) = \begin{bmatrix} a_{mj}(0) & & \vdots & \\ \vdots & & & \\ a_{mj}(L_a-1) & \ddots & 0 & \\ 0 & \ddots & a_{mj}(0) & \\ & & \vdots & \\ \vdots & & a_{mj}(L_a-1) \end{bmatrix} \quad (1.23)$$

Elements $A_m(j)$ operate on (by left multiplication), and conform to, column vectors that are the estimated impulse responses hmn. Equivalently, these convolution operators filter the retrospective transmit waveforms through the linear system defined by the estimated impulse response hmn for the transmit-receive channel pair of interest. Each retrospective transmit waveform contains relative inter-transmit-element delays set by the desired focus point of the retrospective transmit event. Typically, the waveforms $a_{mj}(t)$ are simply a Dirac delta function, delayed as needed for beam-steering by a fractional delay filter. However, variant applications are disclosed in the sequel that utilize high-complexity waveforms in retrospective transmission.

The receive beamforming operators b(j,n) operate on the results of convolutions $A(j)H_n$, to align the retrospective acquisition data from receive channels $[1, \ldots, n, \ldots, N]$. The aligned data is then summed as the pixel value. The alignment operator, vector b(j,n), is comprised of a fractional delay interpolator suitably positioned to a bulk integer delay by zero-padding, so that $$b(j,n) = \begin{bmatrix} \underbrace{0 \ldots 0}_{\lfloor D(n,j) \rfloor^{zeros}} & b_1(d\{n,j\}) & \ldots & b_{L_6}(d\{n,j\}) & 0 & \ldots \end{bmatrix} \quad (1.24)$$

where the beamformer delay D(n,j) for the n-th receive channel is the sum of a fractional delay d(n,j) and an integer delay floor[D(n,j)]. In cascade, in the case of retrospective transmit waveforms chosen to be Dirac delta functions, the operators A and b thus simply extract interpolated values of the impulse response of each transmit-receive channel pair, at lag indices indicated by the round-trip delay of the transmit-receive focus point of the j-th pixel under construction.

Delay parameters $D_T(m,j)$ and $D_R(n,j)$, important to the retrospective transmit-receive acquisition and beamforming for the j-th pixel, are defined graphically in FIG. 3. The figure schematically relates the relevant transducer element-to-pixel signal delays to corresponding lags in the n-th receive channel impulse response estimate set $H_n$.

A given nominal lag index 1 is related to the delay time D by $l=F_S D$. For non-integer lags (usually the case), fractional interpolation filters, or alternately a suitable oversample scheme, must be used. In FIG. 3, retrospective SAIF beamforming of pixel j, implemented on the impulse response estimate data H, means that the retrospective waveform on transmit element $m_1$ needs a relative delay of $D_T(m_1,j)$ when mapped into the A( ) matrix. The retrospective transmit waveform at element $m_2$ is mapped analogously into the A( ) matrix. Correspondingly, data for the retrospective receive beamforming signal component due to element n is delayed by $D_R(n,j)$ through the appropriate interpolation filter mapped into b(n).

The architecture of the basic B-Mode grayscale imaging algorithm is shown in FIG. 2.

E. Implementing the Computation

Three methods for implementing the computation algorithm are outlined here. Two are based on precomputed and stored linear filters, while the third is based on iterative linear system solver technology. The impulse-response estimation step of the proposed algorithm, constituting the vast majority of the computation required, is executed independently for each receive channel in the computation methods suggested here. This provides a natural partitioning for multi-processors with memory having multiple read channels. This method is implements on a computing system utilizing, among other things, a microprocessor and memory, typically associated with ultrasound imaging equipment.

The first method utilizes precomputed filters that is a stored version of the pseudoinverse of the augmented X matrix in (1.17) for a given regularization parameter choice. In practice the components of this matrix can be stored with compression by truncation of elements below a certain magnitude to zero, where the truncation is relative to the maximum of a row. Typical compression rates for this approach are 10:1 or better. The resulting stored matrix is applied to the entire set of received data, independently for each receive channel n, producing the set of all impulse responses $h_n$ for receive channel n, at each application of the inverse matrix:

$$\hat{h}_n = X_a^+ r \tag{1.25}$$

$$h_n = [h_{1n}; | | ; h_{Mn}] \tag{1.26}$$

where in principle $X_a^+$ can be computed by the Moore-Penrose pseudoinverse.

Filter Computation Method I

A method to compute rows of $X_a^+$, and thus use them as filters, is to solve the underdetermined least square problems $$\mathrm{argmin}\|g_l\|_2^2 \, s.t. \, X_a' g_l = i_l \tag{1.27}$$

for $l=[1, \ldots, ML]$, where $g_l$ is the filter needed to compute the l-th lag in the parameter of vector $h_n$, and $i_l$ denotes the indicator vector. Here we have interpreted $g_l$ to be a function of the estimate $h_n$, so the method giving the solution formulation above is well-known in Gauss-Markov estimation theory [8, Sec. 3.2.2].

Filter Computation Method II

A second method for storing precomputed filters is to design the coefficients to directly compute the n-th receive channel component summand of the beamformed computation of the image's j-th pixel, F(j), using the formulation (1.20). Again interpreting the filter B(n,j)A(j) to be a function of the estimate vector hn, the product $B(n,j)A(j)h_n$, is then equated to the filtering $$g \, E(r) = gXh, \tag{1.28}$$

so that similarly to (1.12) we get another underdetermined least squares problem, $$\mathrm{argmin}\|g_l\|_2^2 \, s.t. \, X_a' g_l = [B(n,j)A(j)]' \tag{1.29}$$

Certain of the disclosed CER architectures interpret the retrospective beamforming as pixel-specific functions of the impulse response lag estimates. This is done in order to invoke estimable function theory, or to construct identifiability constraints in order to reduce bias in the impulse response estimates or otherwise eliminate the use of regularization. Success in these approaches will improve the contrast resolution of the resulting images by reducing bias-induced clutter. In the case of identifiability constraints, the impulse response set may be sequentially estimated, first in the unconstrained setting for the entire image, then as per-pixel refinements by updating the estimates with the constraint correction.

On-Line Solution Method

A third method to compute the impulse response set hn is to execute an on-line solution to the problem using iterative linear system solver technology (LSQR) available in the numerical analysis literature. These algorithms are designed to exploit sparsity and structure in system the system matrix X. Their efficacy hinges on the existence of efficient means to compute products of the form Xy and X'z, where general vectors y and z conform to h and r respectively. In the case of this paper, the X is sparse and block-Toeplitz structure, so therefore has means for efficient computation and parsimonious specification as a linear, time-invariant filter with $N_c$ bits of coefficients per transmit channel per PRI. For a discussion on applying LSQR to estimate time-varying acoustic impulse response models using appropriate preconditioning techniques and avoiding explicit formation of normal equations or covariance matrices.

Regarding "offline" computations executed to evaluate the techniques presented throughout this paper, or to implement offline design tasks, note that the great majority of matrices specified have a high degree of sparsity, or a combination of structure and sparsity. Because of this, sparse linear algebra libraries (such as available in numerical computing environments such as MatLab) may be employed effectively with workstation-class computing resources.

F. Motivation and Analysis of the Algorithm

We describe a motivation for the algorithm, based on the goal of marrying the spatial resolution qualities of synthetic aperture ideally-focused imaging with the sensitivity and low-MI advantages of coded excitation imaging, while exceeding the frame rates needed for dynamic-receive focus rayline-based beamforming.

Consider the synthetic aperture ideally-focused delay-and sum imaging method applied to an array of M elements, where each element is excited individually. This requires an ensemble of M acquisition events to gather the entire RF data set for creation of an image. If the excitation of each element is interpreted as a Kronecker delta function modulating a prototype pulse shape appropriate for the transducer bandwidth, the received data model is identical to that of (1.4) and (1.2) with $x_{mk}(t)$ specified in the trivial case of the excitation code vector being a single symbol with value unity. The resulting model matrix X in this case is the identity matrix.

Thus the SAIF algorithm executes a trivial version of the impulse response estimation, and though with minimal noise rejection performance, results in the same expected estimate $E[\hat{h}_{mn}]$ in (1.14); then given a retrospective acquisition and beamforming design $B(n,j)A(n,j)$ for the j-th image pixel $F(j)$, Gauss-Markov theory shows that the best linear unbiased estimate (BLUE) of $F(j)$ is the function $B(n,j)A(n,j)h_n$, of the BLUE-optimal estimate for the impulse response $h_n$. The task, then, is to determine the best means to estimate $h_n$, and subsequently the pixel as $B(n,j)A(n,j)h_n$. It can be shown that for a limited transmit voltage level, increasing the code length increases the transmit power and decreases the IR estimate variance, compared to conventional SAIF imaging. Conversely, maintaining a constant reference transmit power level while decreasing the transmit voltage and increasing the code length, decreases the mechanical index throughout the imaging region of the tissue, while maintaining sensitivity.

Coded excitation thus enables increased sensitivity against noise in a given imaging scheme defined by [B,A], while maintaining the method's expected point spread function and related deterministic imaging properties.

G. Code Design Considerations

The code sequences generated by random Bernoulli trials produce full rank model matrices X. However, in principle it is possible for random realizations of codes (more so for shorter burst length $N_C$) to have poor estimation properties, as indicated by the diagonal of the inverse Grammian matrix $(X'X)^{-1}$. Equivalently, the condition number of the model matrix X may be poor. By this means, candidate codes realized from Bernoulli trials can be assessed for statistical efficiency, and the best chosen for implementation.

H. Impulse Response Model Variants

The impulse response estimation step, as defined in Section II.C, requires a defined convolution model representing action of the transmitted sequence on the imaged medium. Depending on statistical assumptions about scattering properties of the imaged medium, and on the imaging application, and subsequently on the specific variant of the imaging algorithm as a whole (outlined in the sequel), of the one or more of several variants of the basic convolution model are useful. This section defines these model variants for a single transmit channel and pulse transmission interval, and therefore the channel and slow-time indices m, n, and k are omitted for clarity.

To generalize to multiple simultaneous transmit elements (or virtual apertures), or to multiple transmission intervals (PRIs), the models are extended by horizontal block structure or vertical block structure respectively, in analogy to the multi-PRI and multi-transmit element models described in (1.8).

Fully-Convolved Deterministic Model

The fully convolved model definition in (1.7), when used in the standard Linear Model (Gauss-Markov), implies a deterministic vector of unknown parameters. As noted in an earlier section, the expectation of the RF measurement vector is $$E(r)=Xh \quad (1.30)$$

where the definition of Toeplitz-structured X is repeated here for convenience as $$X = \begin{bmatrix} x(L_x-1) & \cdots & x(0) & 0 & \cdots & 0 \\ 0 & & & \ddots & & \vdots \\ \vdots & \ddots & & & \ddots & 0 \\ 0 & \cdots & 0 & x(L_x-1) & \cdots & x(0) \end{bmatrix}. \quad (1.31)$$

The model above is appropriate for unbiased estimation of a finite segment of a non-causal impulse response. In the problem at hand, this corresponds to a window of RF measurements beginning when the receiver's transmit blanking ends, and terminating at the final RF sample of the acquisition event. This implies the true impulse response is assumed to have infinite time support, while the transmitted data is of finite support. To help visualize the layout of the data in the model components X and h (the product of which forms the RF data measurement), the matrix formulation is illustrated schematically in FIG. 4.

Stochastic Impulse Response Model

One way to extend this model to stochastic (random) flow parameters, while retaining the Linear Model and subsequent least-squares solution method, is to vertically augment the impulse response model matrix by additional rows in the form of a scaled identity matrix. Correspondingly, the RF measurement vector (observation) r is augmented by a conforming vector of zeros, defining the augmented measurement $r_n^{Aug}$. The resulting augmented system is then $$r_n^{Aug} = \begin{bmatrix} r_n \\ 0 \end{bmatrix} = \begin{bmatrix} X \\ \alpha I \end{bmatrix} h_n \quad (1.32)$$

The scaling parameter $\alpha$ is equivalently a regularization parameter, in the non-stochastic interpretation, and a variance parameter otherwise. The stochastic interpretation leads to the Wiener filter problem], or equivalently the regression model. The purpose of formulating the problem as an augmented system is that then the parameter vector can be treated mathematically as deterministic, allowing a standard least-squares formulation of the solution. One benefit of the regularization formulation above is that it allows the direct use of least squares solution methods, and analysis of the basic linear model. For additional flexibility in penalizing impulse response lags, the alpha-scaled identity matrix above can be generalized to a diagonal matrix with separated weighting corresponding to different impulse response lags, so that $$\begin{bmatrix} r_n \\ 0 \end{bmatrix} = \begin{bmatrix} X \\ \begin{pmatrix} \alpha_1 & & 0 \\ & \ddots & \\ 0 & & \alpha_n \end{pmatrix} \end{bmatrix} h_n \quad (1.33)$$

This allows treatment of some lags values of h as deterministic (zero weighting) and others as stochastic (non-zero weighting).

Heterogeneous (Mixed-Effects) Model

In another variant, the impulse response convolution model is partitioned into deterministic and stochastic components. In the following, we assume a simplifying approximation that the flow signal has been isolated by stationary tissue rejection, processed over a longer time interval than the support of the mixed-effects model. In the current context, the model will be applied to a limited subset of acquisition events or PRIs. Therefore, the model will be indexed for a single PRI k, though a larger subset of PRIs can be used (The topic will be discussed in more detail in Sections III.C and III.D). The following development of combined deterministic and stochastic terms is known in the estimation and statistics literature as the mixed-effects model [8]. For the components of a single transmit channel m and PRI k, the convolution matrix $X_{mk}$ in (1.7) and impulse response $h_{mk}$ are partitioned as $$X_{mk} = [X_{mk}^F | X_{mk}^M | X_{mk}^B], \quad (1.34)$$

$$h_{mk} = [h_{mk}^{F\prime} | h_{mk}^{M\prime} | h_{mk}^{B\prime}]', \quad (1.35)$$

and for convenience $$h_{mk}^A \triangleq [h_{mk}^{F\prime} | h_{mk}^{B\prime}]', \quad (1.36)$$

where the superscripts F, M, and B on $X_{mk}$ indicate front, middle, and back, respectively, where the middle term represents deterministic components due to scattering from the desired signal-of-interest pixels, as embedded in their associated impulse response lags; and terms labeled front and back represent stochastic signals embedded in lags associated with regions adjacent to the pixels of interest. The term $h^A$ collects all lags adjacent to the central lag segment $h^M$. The block components of $X_{mk}$ are defined as $$X_{mk}^F = \begin{bmatrix} x_{mk}(L_x-1) & \cdots & x_{mk}(0) & 0 & \cdots & 0 \\ 0 & & & \ddots & & \vdots \\ & \ddots & & \ddots & & 0 \\ & & & & & x_{mk}(0) \\ \vdots & & \ddots & & & \vdots \\ & & & & & x_{mk}(L_x-1) \\ & & 0 & & & 0 \\ & & & & & \vdots \\ 0 & & \cdots & & & 0 \end{bmatrix}, \quad (1.37)$$

$$X_{mk}^B = \begin{bmatrix} 0 & & \cdots & & 0 \\ \vdots & & & & \\ 0 & & \ddots & & \vdots \\ x_{mk}(0) & & & & \\ \vdots & & & \ddots & 0 \\ x_{mk}(L_x-1) & 0 & & & \vdots \\ 0 & \ddots & \ddots & & \\ \vdots & \ddots & \ddots & & 0 \\ 0 & \cdots & 0 & x_{mk}(L_x-1) & \cdots & x_{mk}(0) \end{bmatrix}, \text{ and} \quad (1.38)$$

$$X_k^M = \begin{bmatrix} 0 & \cdots & 0 \\ \vdots & & \\ 0 & & \\ x_{mk}(0) & & \vdots \\ \vdots & & \\ x_{mk}(L_x-1) & \ddots & 0 \\ 0 & \ddots & x_{mk}(0) \\ & & \vdots \\ \vdots & & x_{mk}(L_x-1) \\ & & 0 \\ & & \vdots \\ 0 & \cdots & 0 \end{bmatrix} \quad (1.39)$$

The number of columns in the deterministic model component matrix block $X_k^M$ has a number of columns equal to the number of deterministic lags being computed. Thus, $X_k^M$ may have as few as a single column, corresponding to a single computed impulse response lag estimate. This means that in the case of the pixel-specific impulse response estimation (Section II.C), the deterministic IR component estimation has favorable degrees-of-freedom conditions, so that the estimation setup is overdetermined for each pixel. Then for a given mixed effects model this leads to the model moment components $$E[r_k] = X_k^M h_k^M \quad (1.40)$$

and $$\text{cov}[r_k] = \Sigma_k^F + \Sigma_k^B + I\sigma_v^2 \quad (1.41)$$

$$\text{cov}[r_k] = X_k^F \Sigma_h^F X_k^{F\prime} + X_k^B \Sigma_h^B X_k^{B\prime} + I\sigma_v^2 \quad (1.42)$$

$$\text{cov}[r_k] = X_k^F X_k^{F\prime} \sigma_h^2 + X_k^B X_k^{B\prime} \sigma_h^2 + I\sigma_v^2 \quad (1.43)$$

where we have made the simplifications $$\Sigma_h^F = \begin{pmatrix} \sigma_h^2(1) & & 0 \\ & \ddots & \\ 0 & & \sigma_h^2(L_F) \end{pmatrix} = I\sigma_v^2 \quad (1.44)$$

with $\sigma_h$ representing a priori (or otherwise anticipated) root variances of scattering contributing to the impulse response lags. The noise floor standard deviation is $\sigma$. In the extreme case, the model component $X^M$ consists of only a single column for the impulse response lag needed for subsequent retrospective TX-RX beamforming of a specific pixel of interest during reconstruction; in this usage, the estimation models (and consequently estimation computations) are pixel-specific. The classical solution of the mixed-model estimation equations [8] is comprised of the deterministic term estimate $$\hat{h}_k^M = [X_k^{M\prime} \Sigma_{rk}^{-1} X_k^M]^{-1} X_k^{M\prime} \Sigma_{rk}^{-1} r_k \quad (1.45)$$

and the stochastic term estimate $$\hat{h}_k^A = \Sigma_{h^A rk} \Sigma_r^{-1} [r_k - X_k^M \hat{h}_k^M] \quad (1.46)$$

where the covariance are defined as $$\Sigma_{h^A rk} = \text{cov}(h^A r_k) \quad (1.47)$$

and $$\Sigma_r = \text{cov}(r_k) \quad (1.48)$$

The matrix formulation is shown schematically in FIG. 5.

High-Doppler Processing

Another convolution model variant allows "Pulse Stacking", or super-scheduled transmissions that issue before the acoustic medium impulse response due to previous transmission has decayed completely. This has application in high-Doppler imaging modes, where blood (or other target-of-interest) velocity exceeds the pulse rate achievable due to acoustic time-of-flight restrictions of the imaged tissue or target position; and for coded excitation, where reflections from distant tissue ensonated during previous transmission interval (PRI) interferes with reflections from imaged tissue ensonated during the current transmission interval. The schematic of the pulse-stacking convolution model, denoted $X^{PS}$, for the case of two-pulse interference (corresponding to a PRF twice that normally achievable according to time of flight) is shown in FIG. 6. In the schematic matrix figures, each diagonal block corresponds to a fully-convolved block of Toeplitz structure, as in the definition of X (1.7).

As shown in FIG. 6, the schematic represents a model for single RF data acquisition (due to a single transmit element), which is affected by the most recent transmitted burst, and the burst previous to that. The RF data measurement in this case corresponds to a single acquisition burst. Generalization of the pulse-stacking model to additional interfering pulses occurs in two layouts. This first is by appending further previous pulses as additional columns of the model $X^{PS}$, which therefore implies extension of further lags to the impulse response vector.

The second method increases the number of RF data used, for the given delay spread considered relevant, leaving the number of h lags unchanged; therefore the number of rows of $X^{PS}$ is increased. The second scenario is illustrated in the schematic of FIG. 7, which observes RF data for two acquisition cycles.

Note in FIG. 7 that the second burst's blanking period (between the two acquisition cycles) has been excised.

Extension to additional simultaneous transmit channels follows the examples of the previous non-pulse-stacking models.

Note that the transitions of receiver blanking between acquired RF data segments indicated, by intersection of those model matrix rows with the transmitted code diagonals of the model matrix, will constitute regions of higher variance in the estimated impulse response lags associated with corresponding model columns intersecting the code diagonals.

The variants to the impulse response models described above will be used as components in descriptions of extensions to the disclosed imaging method, shown in Section III below.

I. Tissue Motion and Doppler

Here the effect of motion in the ensonated media (tissue or blood) is addressed by modeling the impulse response components in a piecewise manner between transmission intervals, i.e., in the slow-time or PRI dimension. In contrast, the models described in earlier sections model a fixed acoustic medium. The described models are parametric in that the impulse responses are computed for a plurality of parameters that are coefficients of basis functions representing an expected range of possible motion dynamics. For example, in the case of second-order polynomial modeling scatterer motion, impulse responses are computed for the mean, linear, and quadratic variations of impulse response lags over the ensemble of pulses. Alternately, a Fourier or sinusoidal basis may be used to model the motion. The resulting impulse response estimate set, parameterized by motion parameters, is used in the retrospective beamforming step as needed to computed Doppler-specific pixel values.

A model for the effect of tissue motion on the impulse response between a transmit element and a receive element is illustrated in FIG. 8. FIG. 8 shows an ellipse on which lies a locus of pixels or scattering centers, all sharing a constant round-trip distance $D_l$ of singly-reflecting propagation paths between the transmit element and receive element. In the case of the transmit acoustic wavefront at the pixel being normal to the line of sight between the transmitter and pixel, motion of scattering at a pixel induces zero Doppler when its velocity direction is tangential to the ellipse. In FIG. 8 this case is denoted $V_{tan}$. Conversely, observed Doppler induced by the scattering motion at a pixel increases at angles of velocity direction that are off the tangent. The relation between the effective incident and reflected wavefront angles, and the velocity vector of the pixel's scattering motion, is described by the bi-static range-rate equation as $$f_{Dopp} = -\frac{1}{\lambda}(n_{TX} - n_{RX}) \cdot v \qquad (1.49)$$

where the scatterer velocity is $v=[v_x, v_z]^T$, and unit vectors $n_{TX}$ and $n_{RX}$ point from transmit element to pixel, and pixel to receive element respectively.

The impulse response lag values $h_{mn}(1)$ are allowed to vary over ensemble by expansion of the model (1.4) with explicit slow-time indices for the h at each PRI. In the case of tissue or "wall" motion, polynomial basis constraints are then introduced to model this time variation over PRI; in analogy to color Doppler wall filter design, other basis functions such as sinusoidal or Fourier basis may be employed similarly. The fitted measurement obtained by the model and estimated IR set can then be interpreted as the component of the signal due to stationary or slowing moving tissue. The process is explained in the following, where we have omitted the receive channel subscript n for clarity. Therefore in this scheme, the impulse response set is expanded to include explicit slow-time (PRI) indices k, $$H=[H_1; \ | \ ;H_K] \qquad (1.50)$$

where $$H=\Pi_P h, \qquad (1.51)$$

with $\Pi_P$ defined in this example of a second-order polynomial basis as $$\Pi_P = \begin{bmatrix} 1 & 1\theta_{11} & 1\theta_{21} \\ \vdots & \vdots & \vdots \\ 1 & 1\theta_{1K} & 1\theta_{2K} \end{bmatrix} = I_T \otimes \Pi_{P1} \qquad (1.52)$$

where the size-T identity matrix $I_T$ is left of the Kronecker product where $$\Pi_{P1} = \begin{bmatrix} 1 & \theta_{11} & \theta_{21} \\ \vdots & \vdots & \vdots \\ 1 & \theta_{1K} & \theta_{1K} \end{bmatrix} \qquad (1.53)$$

is dimensioned [K×(P+1)], with p-th column $\pi_p$ as $$\pi_p=[(-K/2)^{p-1}, \ldots ,(K/2)^{p-1}]^T, \qquad (1.54)$$

and where the generalized impulse response h includes the components for the fixed, linear, and quadratic terms.

Note that the polynomial basis matrices should be normalized for numerical conditioning. Higher order polynomials would model the tissue motion by straightforward extension of the matrix $\Pi_P$ above with additional block columns.

In the case of sinusoidal or Fourier basis functions modeling the motion, the coefficient matrix is, similarly to $\Pi_P$, $$\Pi_F = \begin{bmatrix} Ie^{-i\Omega_1 t_1} & \ldots & Ie^{-i\Omega_P t_1} \\ \vdots & & \vdots \\ Ie^{-i\Omega_1 t_K} & \ldots & Ie^{-i\Omega_P t_K} \end{bmatrix} = I_T \otimes \Pi_{F1} \qquad (1.55)$$

where frequencies $\Omega_p$ include a range sufficient to model the motion over the expected range of frequencies, and where $$\Pi_{F1} = \begin{bmatrix} e^{-i\Omega_1 t_1} & \ldots & e^{-i\Omega_P t_1} \\ \vdots & & \vdots \\ e^{-i\Omega_1 t_K} & \ldots & e^{-i\Omega_P t_K} \end{bmatrix} \qquad (1.56)$$

has Fourier basis vectors for columns. Note that for low-Doppler (low-velocity) motion, an impulse response estimate $\Gamma$ that assumes the polynomial basis $\Pi_P$ as a model may approximate a Fourier basis $\Omega$ by the relation $$\Omega=[\Pi_F^T \Pi_F]^{-1}\Pi_F^T\Pi_P\Gamma \qquad (1.57)$$

With these definitions, the system impulse response model for receive channel n is $$E(r_n) = \bar{X} H_n = \bar{X} \Pi h_n \quad (1.58)$$

with $$\bar{X} = \begin{pmatrix} X_1 & & 0 \\ & \ddots & \\ 0 & & X_K \end{pmatrix}, \quad (1.59)$$

where $$X_k = [X_{1k}, \ldots, X_{Mk}]. \quad (1.60)$$

These models of slow-time (PRI) variation for the impulse response lags will be used in Sections III.C, III.D, III.E, and III.L, to achieve stationary tissue signal rejection and motion estimation for flow estimation, tissue motion estimation, and shear wave imaging.

J. Transmit Aperture Designs

The choice of transmitter elements affects the solution of the impulse response estimation equations, and the structure of the retrospective transmit-receive beamforming in the reconstruction step. The design choices in ensemble length, transmit aperture design, and number of transmit channels affect dimensionality and numerical rank of the resulting model defining the impulse responses. Thus the estimation framework may be either over-determined or under-determined. Shown below are several examples of transmit aperture designs.

An example configuration of sparse transmit elements applicable to CER imaging is shown in 9.

FIG. 10 shows an example of sparse transmit elements with extended subapertures, treated in CER beamforming with the position of the reference element. This approach allows reduction in power spatial density, and an amount of directivity to narrow the field of view and reduce clutter:

FIG. 11 shows a CER-compatible sparse extended transmit aperture with elements transmitting shaded and/or steered circular wavefronts generated from virtual apex sources. Retrospective beamforming reference the virtual apex locations for relevant timing information. This allows increased rejection of scattering from outside the desired field of view.

III. Extensions to the Algorithm

This section describes several variations to the algorithm effective in various imaging modalities, including B-Scan, Color Doppler Imaging, Quantitation Multi-point Spectral Doppler, tissue motion imaging, shear wave imaging, and their 3-D variants.

The disclosed algorithm and its variants enable these imaging modes to be executed with better clutter, sidelobe, and sensitivity performance compared to other techniques A. Retrospective Imaging on Impulse Response Estimates from Coded Excitation Transmissions on Simultaneous Elements The disclosed two-step Coded Excitation Reconstruction method, consisting of an impulse response estimation step based on physical transceiver operation on the physical medium, followed by a beamforming step based on virtual transceiver operation on the impulse response estimates, has the several advantages over other transmit-receive beamforming methods. (1) Lower mechanical index for equivalent energy per frame; (2) Lower energy per frame for the same pixel SNR; (3) conversion of coded transmission acquisition data using many cycles per transmission, into the same expected responses as from a synthetic aperture scheme using short pulses; (4) simultaneous acoustic probing of the medium by all utilized transmit elements; (5) simultaneous illumination of the entire field-of-interest by all transmit elements; (6) identical, independent processing of receive channels for the estimation step of the algorithm, comprising the large bulk of computation cost, therefore favoring channel-based computation architecture.

High Framerate, Wide FOV or Deep Imaging with Improved Contrast Resolution for Linear and Phased-Array Transducers High framerate, wide field-of-view (FOV) and/or deep imaging regimes with linear or phased-array transducers, with improved contrast resolution over conventional imaging, are enabled with the disclosed algorithm CER by judicious selection of transmit elements and virtual source synthesis. For increased frame-rates, fewer virtual transmit elements are used.

Small Physical Transmit Element Imaging by Coded Excitation.

By means of the CER imaging technique disclosed, in combination with sufficiently long transmit codes, acoustic power levels sufficient for imaging are achieved with very small apertures containing as few as a single transmit element, at low areal power density or flux.

CIR Estimation Step as a Preprocessor for Virtually any Conventional Beamforming.

The disclosed impulse response estimation technique may be applied as a preprocessing step to virtually any transmit-receive beamforming or reconstruction technique applied retrospectively, subject to certain restrictions. The retrospective transmit-receive reconstruction is applicable to the impulse response set generated by using it as a model for hypothetical transmissions. The impulse response set is indexed by lag index, receive element index, by transmit element (or virtual transmit element) engaged at physical transmit, and by time (if so modeled). Restrictions during retrospective transmit-receive reconstruction are therefore the bounds to those available indices.

The advantage of preprocessing the transmit-receive beamforming, by issuing a series of probing sequences, estimating the medium impulse responses, and using them as inputs to the retrospective transmit-receive beamforming imaging method at hand, is to provide the imagine with the best possible data, in terms of additive noise. This assertion is proved by invoking the Gauss-Markov theorem [8] on the retrospective imaging method operating on the estimated impulse responses: (1) the estimated impulse responses are optimal in terms of estimation variance, given the transmitted probing sequence; (2) the retrospective transmit-receive beamforming is seen to be a function of the estimated impulse responses; (3) beamformed pixels are thus BLUE-optimal estimates by the Gauss-Markov theorem.

One feature of the disclosed method is that it enables the generation of images that are equal in mean to synthetic aperture ideal focus images, but with the transmission of coded waveforms.

The expected performance benefits of this method to image quality, in terms of the statistical mean image (when thermal noise is averaged to insignificance on non-moving targets), are identical to those of synthetic aperture ideal focus imaging. These benefits are primarily seen in the metrics of point-spread function sidelobe reduction, and contrast resolution or clutter reduction. Visually, an immediate perception is that the image will be in focus on transmit as well as receive everywhere in the computed image space.

The expected performance benefit of the disclosed method, in terms of frame rate due to amortization of acoustic acquisition events over slow-time (PRI or ensemble time) and over transmit element (or transmit virtual aperture), depends on transmit level constraints. The transmit level constraints include, at least, (1) transmit voltage due to transducer device destructive limits, (2) transmit power due to acoustic power limits for patient safety or protection of the imaged medium, and (3) acoustic intensity or mechanical index limits for patient safety or protection of the imaged medium. If two imaging methods are compared, their respective limits must be equated with identical pixel SNR in order to obtain a frame rate comparison. Under the assumption of deterministic scattering, the pixel SNR can be determined from the mean and variance of the expression for the computed pixel F(j) in equation (1.19) in Section II.D. To execute this computation, the conventional imaging method being compared to must be put into the form of (1.19). This can readily be accomplished, for example with conventional SAIF imaging, by observing that the transmission of single pulses on individual channels in separate events is a trivially degenerate case of the disclosed method (i.e., produces the identity matrix for single channel convolution models). These statistics are computed readily per standard linear model theory as a function of a linear model estimate [8]. As a rough rule of thumb, it will usually be the case that for equal transmit voltage, conventional SAIF imaging will achieve the same SNR as the disclosed CER-SAIF method by requiring a factor of Nc more transmissions, where Nc is the code length. Thus a rough rule of thumb is that CER-SAIF will be Nc times faster than conventional SAIF in terms of framerate. The speed comparison of the other transmit constraints can be computed similarly for other conventional imaging modes, such as Dynamic Focus (DF). However, the inferior performance of DF in terms of clutter or contrast resolution at pixels distant from the focus should be taken into account by a measure of signal-to-clutter ratio, since clutter is a deterministic effect with may dominant image quality over the effects of thermal noise.

Another feature of the disclosed method is the achievement of a static transmit aperture geometry. The benefit of this is that image information collected due to the extent of the transmit aperture is available for the entire ensemble time interval. When the imaged medium is in motion, conventional SAIF only interrogates the medium at a specific pulse time (PRI) for a given target position. Thus, the point-spread-function benefits of conventional synthetic aperture (sidelobe reduction and contrast resolution) are not available for moving targets. However, by appropriate Doppler or flow processing, these benefits can be exploited by CER-SAIF.

The first processing stage of the disclosed methods is channel-oriented and lag-oriented, rather than pixel-oriented or focal-point oriented.

An advantage with this processing is that two-dimensional (2-D) or three-dimensional (3-D) motion is collapsed onto a one-dimensional bistatic range-rate or Doppler axis. This restricts the Doppler processing and sub-band processing, required respectively to compensate for range phase and range walk in the case of rapidly moving targets, to a single dimension. This is true for both 2-D and 3-D imaging.

B. Extension: Grating Lobe Reduction and Phased-Array Operation with Lambda-Pitched Transducers Large time-bandwidth products possible with coded-excitation waveforms enables usable acoustic penetration to depths that would require phased-array (half-wavelength pitch array) imaging with conventional beamforming. Grating lobe effects are reduced by use of the CER imaging technique. The benefit of this is employment of a larger physical transducer aperture for a given number of elements. This in turn enables enhanced lateral resolution and commensurate improvement in image quality.

C. Extension: Stationary Tissue Rejection (STR) and Doppler Processing

The Coded Excitation Reconstruction (CER) algorithm is extended here to remove stationary tissue signals from the receiver data for Doppler processing.

In this scheme, the impulse responses $h_n$ are allowed to vary slowly over ensemble by expansion of the model (1.4) with explicit slow-time indices for the $h_n$ at each PRI. Polynomial basis constraints are then introduced to model this time variation over PRI; in analogy to color Doppler wall filter design, other basis functions such as sinusoidal or Fourier basis may be employed similarly [15]. The fitted measurement obtained by the model and estimated IR set can then be interpreted as the component of the signal due to stationary or slowing moving tissue. The process is discussed in Section II.I.

Adopting the slow-time (PRI index) impulse response evolution description from Section II.I, the RF measurements are assumed be dominated by slowly moving tissue signal, and to have the expectation $$E(r_n) = \overline{X} H_n = \overline{X}\Pi h_n \tag{1.61}$$

with $$H_n \triangleq \Pi h_n \tag{1.62}$$

and $$\overline{X} = \begin{pmatrix} X_1 & & 0 \\ & \ddots & \\ 0 & & X_K \end{pmatrix}, \tag{1.63}$$

and (in the simplest version) having identity measurement covariance so that basic least squares can be used to solve by direct extension of Section II.C, for example by the pseudoinverse (1.14), giving the estimated impulse response set $\hat{h}_n$. Note that these $\hat{h}_n$ are in the form of coefficients for the time-evolution basis functions; to obtain the time-domain version of the impulse response estimate lags, compute the operation H=Πh. If the technique of mixed effects models (Section II.H) is used, knowledge of scattering power constituting the impulse response lag values enables whitened computation of the wall tissue impulse response.

From the above, the estimates $H_n$ are used with the model $\overline{X}$ to predict the slowly-moving stationary tissue RF signal, and subtract it from the received data r to generate the residual $\tilde{r}$, which will be used as an estimate of flow RF signal.

It is advantageous to note that the fitted measurement $$r = \overline{X}\Pi_p \hat{h}_n \tag{1.64}$$

will be an unbiased estimate of the measurement r, even if the model $\overline{X}\Pi_p$ is not of full rank, as long as the impulse response $\hat{h}_n$ is computed by a generalized inverse (such as the Moore-Penrose pseudoinverse). This is because the fitted measurement always constitutes an estimable function; see [8] for more discussion. The implication of recognizing this is more flexibility in the designing ensemble length, polynomial or Fourier model order, and number transmit aperture elements, while achieving wall signal rejection for subsequent Doppler processing.

The residual r̃ then, in analogy to conventional color Doppler wall filtering [15], is interpreted as containing primarily the signal components due to scattering from blood, or other rapidly moving tissue, corrupted by noise. The bulk of the stationary tissue signal has been thus removed from received RF signal. Here we denote this as the received RF flow estimate. The RF flow estimate is then processed by one of several methods described in the sequel, to accomplish beamforming of the flow signal, or simultaneous beamforming and Doppler or velocity filtering.

Residuals Processed by Matched Filter Doppler Processing

In this variant of the algorithm, the residual signal containing flow data is not further processed by the CER algorithm. The residuals are simply processed by conventional pulse-compression matched-filter or matched-field processing to yield beamforming of the flow signal. Here, the transmitted codes are used to define matched filters for the expected signature at each pixel, due to the geometry of delay paths from each code-transmitting array element to the pixel of interest. These matched filters are then applied to the receive channel data at the appropriate times for receive beamforming of the specific pixel. The process is repeated for each PRI independently to produce a series of images, which is then processed for Doppler information at each pixel. Contrast resolution problems typical of matched-filter pulse compression schemes will be reduced, because the flow signal is typically spatially sparse in many applications.

Residuals Processed by CER with Fourier Time Model

In another residual-processing scheme for generating flow imagery, the flow signal contained in the residual signal r̃ described above is processed by a second CER impulse response estimation operation, to extract the impulse response set corresponding to only the flow signals present. In this secondary flow processing stage, a Fourier basis is used to model the time-evolution of the impulse response lags over the PRIs in the ensemble. With this approach, the retrospective beamforming is applied to a spectrum of computed impulse response sets, comprised of an impulse response set for each Fourier Doppler frequency.

Here, in the secondary CER estimation of flow signal impulse responses, the columns in the polynomial model Π described above are replaced with one or more Fourier basis vectors. These are sampled at the PRF, and supported over the ensemble time. This enables estimation of the impulse response set corresponding to scattering with motion commensurate with the Fourier frequency of the basis vector(s), in analogy to the wall motion tissue signals modeled by polynomials in the STR processing stage. The Fourier impulse response components may be regularized by augmentation of the model as described earlier in Section II.C. Then, by processing repeatedly over a range of Fourier frequencies spanning the Doppler frequencies of interest, an impulse response estimate set is generated for each Doppler frequency. The impulse response estimates associated with the Fourier components are then each processed by retrospective imaging method II.D to yield an image for each Fourier frequency, forming a Fourier spectrum of images. A suitable subset of these is processed for display as the color Doppler modality image information. Likewise, one or more pixels are selected to provide spectrogram trace displays over multiple frames in the Spectral Doppler modality.

In the above methods, computation of the stationary tissue (or "wall") signal estimate by least squares solution of the polynomial (or otherwise low-rank) basis parameters is suboptimal in that while unbiased, may not provide minimum variance estimates. This is because the flow signal may not be white, as in the case of a single (or otherwise incomplete collection of) Fourier coefficient(s). With assumptions on estimated flow parameter variance components, then these may be used to compute the appropriate whitening matrix to compute the optimal weighted least squares estimates of the wall signal impulse responses. In many imaging applications, the previously computed image frames often contain information representative of the current image frame under computation. In this case estimation of the variance components is feasible and can provide for weighted least squares computation of the current frame wall signal impulse responses.

Joint Model

In a variant of the single approach, the CER processing producing the stationary tissue signal impulse responses and the flow signal impulse responses are computed jointly in a single stage. This is accomplished by appending the Fourier flow signal model to the polynomial wall signal model, producing a combined model for the time evolution of the impulse response values at each lag. The implication here is that no prior assumptions about flow power are taken.

In another residual-processing scheme for generating flow images, the single-Fourier basis concept above is extended to the entire Fourier basis. The resulting model is regularized by including the Fourier estimate vector energy as an additional penalty in the least-squares residual by an appropriately weighted identity matrix appended to the convolutional model X̄.

In this way, coded excitation imaging is utilized for color Doppler imaging, with commensurate gains in sensitivity and/or mechanical index reduction, without compromising sidelobes performance or contrast resolution as typical in traditional matched-filter pulse compression of coded excitation acquisition schemes. The above techniques may be especially applicable to weak-signal, low-Doppler flow scenarios.

The disclosed algorithm variants enable high-framerate, multi-point, quantitative spectral Doppler with more effective clutter, sidelobe, and sensitivity performance compared to other techniques. Table [table-arch-lowflow] below shows an outline of the impulse response estimation algorithm steps for the residual processing methods shown above.

Narrowband Processing Variant

In situations with significant scatter motion velocities or higher-Doppler frequencies, scatterer migration between impulse response lags can be addressed by transforming the computed impulse response lags' frequency spectra into the time domain by inverse Fourier transform. This step is demonstrated in FIG. 12, in the transition from the left panels to the middle panels. From these are computed an image sequence by the retrospective acquisition and beamforming method of Section II.D. The images' pixel time sequences are then processed with conventional Color processing such as Kasai autocorrelation. Another method to handle the high-Doppler case is to implement a sub-band processing scheme. Here, the first step is to narrowband the RF data in the fast time (RF sample time) dimension, and process each analysis sub-band separately. This keeps the scatterers within an axial resolution cell for a larger number of PRI or acquisition cycles than would be the case for direct.

Another narrowbanding scheme may be also accomplished on the received data by a sub-band decomposition filter bank. Each analysis sub-band is then processed, per the CER STR/Doppler method, to compute the estimated impulse response slow-time sequence for each sub-band. The wideband impulse response set is then reconstructed from the sub-band set, using appropriate synthesis filters complementary to the decomposition/analysis filters. The resulting wideband impulse response sequence set is then processed per Section II.D for retrospective acquisition and beamforming, to reconstruct the flow image sequence. The flow image sequence can then be processed pixel-wise for Doppler modes such as color Doppler imaging, for example by Kasai autocorrelation processing.

TABLE 2

Algorithm steps for CER impulse response estimation of blood flow

| Signal Regime | Model | Assumptions |
|---|---|---|
| tissue or wall signal | $r = X\Pi_P h_W + X\Pi_F h_F + e$<br>$E\{r\} = X\Pi_P h_W$<br>L.S. → $\hat{h}_W$ | Unbiased wall signal model, stochastic flow<br>$\sigma^2 \Box \, E\{\|h_F\|^2\}$ |
| wall signal | W.L.S. → $\hat{h}_W$ | $E\{h_F\} = 0$<br>cov$\{h_F\}$ known |
| estimated RF wall signal | $\hat{r} = X\Pi_P \hat{h}_W$ | |
| residual | $r_F - e = \tilde{r} = \hat{r} - r$ | |
| flow signal | $r_F = X\Pi_F h_F + e$<br>cov$\{r_F\} = X\Pi_F \Pi_F' X' \sigma_F^2 + I\sigma^2$ | regression interpretation |
| flow signal | $r_F = \begin{bmatrix} X\Pi_F h_F \\ I\sigma/\sigma_F \end{bmatrix} + u$ | Tikhonov interpretation |
| Fourier domain | L.S. → $\hat{h}_F^{\Omega}(\omega_k)$ | |
| Time domain | DFT$^{-1}$ → $\hat{h}_F(t)_{t=kPRI}$ | |

Demonstrative Example (Shear-Wave Imaging Scenario)

The algorithm is demonstrated on controlled data in FIG. 12, for the case of two transmit elements and a single receive channel with 48-cycle codes, and two scattering centers with contrary motion at approximately ⅓ Nyquist velocity over 12 pulse repetition intervals. The algorithm uses a full Fourier basis and shows impulse response estimates peaking at a specific bin in the Fourier domain corresponding to scattering motion respective to each transmit element.

D. Extension: RF-Domain STR and Subsequent Heterogeneous Model for Beamforming Doppler Components This variant of the disclosed algorithm allow Doppler processing with greatly reduced transmissions per image frame, compared to conventional multi-beam imaging schemes. In this scheme, the heterogeneous (mixed-effects) impulse response model is used. Heterogeneity in IR convolution models between the STR IR estimation step and flow IR estimation step allows un-regularized (and hence low bias) stationary tissue rejection, followed by regularized (and hence low-noise) IR estimation and subsequent imaging of flow signal.

The impulse response model is heterogeneous in that it takes two distinct forms: one form for the STR step, and another form for the flow IR estimation step. The STR step is as described in Section II.C. In the STR step, the IR convolution model is low-rank in the time dimension and critically-determined (per PRI), leading to a well-conditioned model for the entire ensemble. Thus the STR step requires no regularization parameters. This allows the measurement residuals to be interpreted as relatively unbiased estimates of the RF flow signal. The STR step can be enhanced by whitening, based on any available a priori flow power distribution information, in conjunction with the stochastic model components of (1.34).

Subsequently, the flow IR estimation step uses the residual RF signal generated by the STR step. The flow IR estimation uses regularized, over-determined IR convolution models, as described in Section II.H under the heading Heterogeneous (Mixed-effects) Model. The acquisition data are partitioned into multiple, separately-processed time-window segments, optionally with time basis weighting appropriate for Doppler frequencies, each with sufficient amounts of regularization. The time window of each flow impulse response estimation station can be as little as a single PRI or acquisition cycle.

Pixel-Specific Impulse-Response Models

For a given image pixel under reconstruction for a given acquisition cycle, pixel-specific impulse response computation is possible. In the case the heterogeneous model presents two choices of processing. In either case, the impulse response lags needed to reconstruct the pixel, per FIG. 3, define the partitioning of $X_{mk}$ to its front, middle, and back portions $X_{mk}^F$, $X_{mk}^M$, and $X_{mk}^B$, of the model in (1.34). The size of $X_{mk}^M$ then defines columns associated with impulse response lags needed for computing the pixel of interest. Thus, denote the IR lags in h associated with columns of $X_{mk}^M$ as the lags of interest. Components $X_{mk}^F$ and $X_{mk}^B$ model extraneous lags not needed for the pixel, but rather needed to model disturbance in the RF measurement due to proximal flow.

The two choices available at this point are to define $X_{mk}^M$ to be stochastic, or to be deterministic. In the former case, the model at this stage becomes the regression model [8], or the Wiener filter in signal processing parlance. In this case, solution requires a parameter for flow signal power relative to the noise floor. This will place a stochastic constraint on the flow estimated for the pixel. In contrast, if $X_{mk}^M$ is assumed deterministic, no constraints are imposed on the energy in the lags-of-interest IR estimates, other than the Toeplitz model structure. In this case, the secondary impulse response estimation becomes a mixed effects model operating on the residuals from the first, STR stage of processing. The mixed effects model components in this case are:

$$r_k = X_k^M h_k^M + X_k^F h_k^F + X_k^B h_k^F + e \tag{1.65}$$

with mean $$E(r_k) = X_k^M h_k^M \tag{1.66}$$

and covariance $$\text{cov}(r_k) = [X_k^F X_k^{F'} + X_k^B X_k^{B'}]\sigma_h^2 + I\sigma^2. \tag{1.67}$$

One approach to solve this model is by the regularization method in (1.32).

With all the pixel-specific impulse response estimation methods, an estimation filter may be computed per the methods described in Section II.E under the headings Filter Computation Method I and II. The resulting filters can be stored in lookup tables. Typically, the filter coefficients have a large percentage of entries that are very small, compared to a few large entries. Hence, high-rate storage compression of the lookup tables is possible.

Since the number of lags-of-interest needed to reconstruct a given pixel are small, the $X_{mk}^M$ can be full-rank (overdetermined) with adequate choice of acquisition parameters, and can be readily estimated per the Best Linear Unbiased criteria for mixed-effects model solution [8].

The method is illustrated in FIG. 13.

Further benefit from successful rejection of stationary tissue during the STR step arises for the following two reasons. First, after STR processing the subsequent flow signal is appropriately modeled as stochastic in nature. This is because realizations of flow RF signal contributed by a given pixel location will be highly varied between transmissions, and yet have a time-averaged modulus that is an apt proxy for flow signal power at the pixel. Second, the flow signal is spatially sparse compared to strongly reflective tissue clutter rejected in the STR phase. These two properties render meaningful the interpretation of regularization as an assumption of prior statistics on the estimated IR parameters during the flow IR estimation stage. Because of this, the selection of effective regularization parameters for flow processing is easier than would case of stationary tissue processing, and can be executed in part by multi-frame noise floor estimation and B-scan processing, and in part by operator selection as a sensitivity or "gain" control scheme.

E. Extension: Sliding Window Reconstruction for Doppler Processing, Shear Wave Imaging, and Tissue Motion Imaging The methods described in Sections II and III can be applied to overlapping segments of multiple RF data acquisition sequences to enable Doppler processing and tissue motion imaging. The method here is termed Sliding-Window Reconstruction (SWR). One feature of this method is that is creates a series of images generated from a static transmit-receive transducer array geometry. That is, the set of transmitter and receiver elements does not change between acquisition events. This means that, subject to the condition that linearly independent transmit codes are employed in the acquisition sequence, the clutter field of stationary tissue in the reconstructed image sequence has expected value that is fixed over different acquisitions. That is, differences in the expected images are due to noise, and not changes in transmit aperture or focusing between different acquisitions.

In the case of blood flow imaging, this method processes the de-trended STR residual with short overlapping segments of PRIs, in a sliding-window fashion, to generate a series of unbiased impulse response estimate sets over the ensemble. This is enabled by the use of a reduced number of transmit elements with the fully convolved, deterministic model, (Section II.H) which allows unbiased impulse response estimates with only a few PRIs per estimate model. This approach can be combined with the polynomial or Fourier basis motion model extensions of Sections II.I, III.C, III.D, and III.F. After retrospective beamforming of the series of impulse response estimates, the resulting image sequence is then processed by conventional color Doppler [7], spectral Doppler, or vector Doppler [19] processing.

In another variant, blood flow imaging is computed by processing the short overlapping segments with the mixed-effects or heterogeneous model of Section II.H. Here, impulse response estimation is conditioned on the specific lags needed for the pixel of interest.

In the case of shear wave imaging or tissue motion imaging, the SWR approach is used without the stationary tissue signal (wall signal) rejection, or STR, processing step.

This algorithm variant enables high-framerate, multi-point, quantitative spectral Doppler with more effective clutter, sidelobe, and sensitivity performance compared to other techniques such as planewave imaging.

F. Extension: Ultra-High Doppler Signal Estimation.

In this variant of the algorithm, the impulse response models are extended for ultra-high Doppler applications to incorporate effects of reverberation, or ghost images, from "pulse-stacking" the acquisitions at a PRF higher than allowed by the acoustic time of flight. The technique has application to cardiac imaging, color Doppler and Spectral Doppler processing, and inter-pulse reverberation clutter reduction, as well as imaging high-speed moving tissue (TMI) or transient phenomena such as shear waves. The method incorporates the models described in Section II.H (Ultra-high Doppler Processing) into the impulse response estimation methods of Section II.C, the retrospective acquisition and beamforming method of Section II.D, and the Doppler/motion estimation and wall signal rejection methods of Sections III.C, III.D, and III.E.

The pulse-stacking modeling approach described in Section II.H enables extended Doppler estimation range by mapping an extended impulse response, containing effects from multiple acquisition bursts, into shorter acquisition RF measurement windows corresponding to a higher-than Nyquist pulse repetition frequency. Because the RF data captured at each acquisition event is modeled fully within the assumptions of reverberation bounds, the disclosed CER methods and its variants for wall signal rejection and Doppler processing are directly applicable.

The penalty incurred in the scheme is receiver blanking at the start of each acquisition burst, and correspondingly at impulse response lags coincident with the transmissions. This leads to an associated proximal increase in impulse response lag estimate variance (noise). However, by judicious choice of PRF, the receiver-blanking regions may be shifted to lags corresponding to pixel depths outside the region of interest (for example, outside the color box in color Doppler applications, or outside the sample volume desired in a spectral Doppler application).

This technique is applicable to BMode imaging as well with very high frame rates. In this way, clutter from ghosting is reduced when the PRF is beyond the acoustic limit based on time-of-flight for the imaged depth.

G. Extension: Tissue Motion Compensation in B-Mode

By the same method described in Sections II.I (Tissue Motion and Doppler) and III.C above (Stationary Tissue Rejection for Doppler Processing), B-Mode (grayscale mode) imaging artifacts due to tissue motion during the ensemble may be reduced. In this approach, motion of those scatterers contributing to impulse response lags of interest are modeled by polynomial basis functions supported in the slow-time (PRI domain) index. After impulse response estimation only the lowest order, constant-term coefficient components of estimate $\hat{h}_n$ are retained for subsequent retrospective acquisition and beamforming, while the higher-order basis components model the motion disturbances, and so contribute to a better fitted estimate. This has application, for example, in cardiac imaging.

H. Extension: Virtual Transmitter Linearization.

Some ultrasonic transceiver operating characteristics behave so as to render the linear model (1.4) inaccurate to a degree that may induce noticeable clutter, noise, or artifacts in computed imagery. These inaccuracies may be non-linear, time-varying, or both. Some of these characteristics include pulser asymmetry; TGC modulation effects; transmit voltage droop or decay over the transmit burst period (or otherwise decay in effective achieved acoustic transmission intensity); nonlinear stress-strain relationship in the transducer; and burst-to-burst variation in the effective level of transmit voltage.

Pulse voltage asymmetry is a difference in shape between pulses of opposite polarity, when the shape difference is not explained by a polarity change. Thus it is a transmit non-linearity because a sign change of the modulating input is not preserved at the transmitter output. Leakage of H-bridge FET drivers through the SEPIC transformer can induce a similar effect. To linearize this effect for Doppler applications, partition the +/−code chips into separate sources in the model, each with independent associated impulse response parameter vectors. Thus the method will double the number of parameters being estimated. This doubling can be mitigated by the following method: the true IR vectors should be identical but of opposite polarity (subject to medium linearity), and except for different transmitter pulse shapes which are embedded by convolution. The embedded pulse shapes should be measurable in a laboratory setting, and usable in-vivo as adjusted amplitude/phase of code chip signs in the conventional single-pulser model. This relation enables linear constraints relating the two parameter estimand vectors, which mitigates estimation noise incurred by doubling the number of estimated CIR parameters. In this model, generalized upsampling interpolation kernels are used when necessary to ensure full rank of the model matrix.

A second linearization process is application of the time-gain-control (TGC) function used during RF channel data acquisition, to the impulse response estimation step. This TGC correction is necessary to mitigate modulation effects on the transmitted data which otherwise are in error according to the basic disclosed model. This correction is accomplished by multiplying the left hand side of the convolution model matrix with the operative TGC curve in the form of a diagonal weighting matrix. Here, the RF observation vector sample time index is collated with the row index of the convolution matrix, so that each row of the convolutional model matrix is weighted by the TGC value at the time the RF sample was digitized. Equivalently, the effect of TGC may instead be removed from the RF data observation vector in the IR estimation step, by simply multiplying the RF data values by the numeric reciprocal of the TGC samples used at capture time. Following estimation and reconstruction, subsequent TGC-like spatial gain control may be then reapplied after the image is reconstructed, prior to mapping to the display colormap range, to enhance visual presentation.

A corresponding whitening adjustment to the entire system (expected measurement equated to model-impulse response product) may be applied, if the TGC curve is known to affect the intensity of thermal or other additive noise seen at the input of the receiver ADC.

In analogy to the TGC correction, a corresponding correction may applied to mitigate effects of transmitter voltage droop over the duration of the transmit event associated with the RF data observation. This effect causes a time-varying decrease in the effective amplitude of the code sequences forming the kernels of the convolutional model. To apply the correction, the droop is modeled and applied as a time-varying decrease in amplitude of the codes before they are used to generate the Toeplitz-structured model matrix. The droop may be modeled by a small number of parameters, applied to the entire transmit element set, and estimated by calibration during transmission of the code by a representative transducer ensonifying a laboratory phantom with nominally equivalent acoustic impedance to in vivo tissue. A correct value of the droop parameter is accepted as that which minimizes the impulse response estimation residuals. Since the droop correction is an unknown multiplicative nuisance parameter, it defines the impulse response estimation step to be an error-in-variables problem, equivalently known as the measurement error problem or the latent variables problem.

Burst-to-burst variation in transmit voltage is mitigated by incorporating a unique, scalar, scale factor associated with the model components each PRI. These scalars are symbolically be factored out of the model at each PRI are divided into the received data separately for each PRI. Thus, iterative improvement may be executed towards the best residual on a fixed model as defined for the particular imaging mode, thereby optimizing corrections for the transmit voltage variation.

I. Extension: Pixel-Specific Transmit Apodization, Weighting, Focusing, or Wave-Shaping Because the impulse response of each transmit-receive channel are resolved in the estimation of Section II.C, during the retrospective acquisition and imaging of Section II.D unique, pixel-specific apodizations may be applied to the retrospective virtual wavefront transmissions. This allows a wider range of tradeoff between peak resolution and contrast resolution, to better optimize the image over depth and width of the field of view, compared to non-retrospective imaging. While this is possible in principle with the elementwise, transmit-synthetic aperture focus scheme SAIF, that scheme suffers in SNR due to its comparatively low transmit power. In an extension to this technique, the weighting on TX and RX is adjusted by metrics including SNR estimates, lag variance estimates, and coherence estimates.

J. Extension: Transmit Subapertures.

The disclosed algorithm readily accommodates, the following types of subapertures: sparse; sparse extended with common transmit drive; sparse extended with common transmit drive modified by delay focusing; and interleaved versions of the above.

K. Extension: Overlapping Simultaneous Wavefront Transmission

In this variant of the disclosed algorithm, the entire array is used to transmit on a virtual element. Multiple virtual transmit elements are simultaneously transmitted per physical acquisition event. Each virtual transmit element is treated in the impulse response estimation step as a distinct source with either a conventional focus point, a virtual apex focus point, a planewave (focus at infinity), a transverse oscillation wavefront, a wide or overlapping beam, or other designed wavefront having a physical or virtual reference point representing a common point in space time for the wavefront origin. This reference point is then used in the retrospective TX-RX beamforming step for appropriate timing information. Simultaneous transmission is achieved by analog/infinite precision design, followed by coding to a tri-state or other limited-precision waveform per the method in J. A. Flynn, "Method And System For Arbitrary Waveform Generation Using A Tri-State Transmit Pulser" U.S. Patent Application PCT/US2014/047080, Jul. 17, 2014. FIG. 14 illustrates the virtual source locations for simultaneous wavefront synthesis.

The benefit of the technique is that it permits large apertures to be available for multiple simultaneous transmission in execution of the primary disclosed algorithm of coded excitation impulse response estimation and retrospective transmit-receive beamforming; this is simply accomplished by modulating the synthesized wavefronts with the desired code sequences, and interpreting each wavefront focus as the virtual transmit element during the retrospective beamforming reconstruction step.

L. Extension: Vector Motion Imaging and Doppler Imaging

The CER methods disclosed enable various Vector motion imaging and analysis modes, and enhanced Spectral Doppler and color Doppler imaging modes.

Vector Motion—Low Flow Regime

Vector Motion imaging, including vector flow imaging, vector shear-wave imaging (SWI), and tissue motion imaging (TMI) are enabled by application of Doppler-indexed (Doppler frequency domain) impulse response estimates generated as in Sections III.C, to the retrospective beamforming steps described in Section II.D and II.I. The approach here is appropriate for lower-velocity or low-flow signal regimes, for example in kidney perfusion, SWI, and TMI. The retrospective beamforming in this case considers Doppler index to be dependent on individual transmit and receive elements indices. In this technique, a range of vector motion values for a pixel is specified. Each of the specified vector velocity values determines, through the range rate geometry illustrated in FIG. 8 and the bistatic range-rate equation (1.49), a set of specific range-rate (Doppler) bins needed for all transmit-receive impulse response components comprising the beamformed pixel. Thus, the retrospective acquisition and beamforming chooses not only the interpolated impulse response lags needed the summation of (1.20), but also their associated Doppler bins as described in Section II.I and III.C. To clarify this, the pixel reconstruction summation of (1.20) is generalized to consider the range-rate (Doppler shift) between each transmit-receive element pair comprising the pixel summation, so that $$F(j,m,n)=b(j,n)A_m(j)\hat{H}_{mn}(f_{Dopp}). \quad (1.68)$$

With this definition, the processing steps are shown in the pseudocode in FIG. 15.

High framerate B-mode imaging, and B-Flow imaging, where imaging of moving blood depends on rejection of stationary tissue, and subsequent time-domain image sequence generation (as described with the techniques disclosed in in Sections III.C, III.D, and III.E) enable vector imaging of flow, tissue, and shear waves by space-time gradient (optical flow) techniques as described in the literature.

Multi-point, retrospective spectral Doppler mode information, quantitative Doppler mode information, and color Doppler imaging mode information, are generated by pixel-specific application of the impulse response estimates generated by the techniques in Sections III.C and III.D, to the retrospective beamforming steps described in Section II.D. In this technique, the vector motion approach described above is approximated by assuming only the z-direction velocity components $v_z$ are significant to the signal phase. This assumption applies in cases of high F-number, such as deep tissue imaging. The assumption then simplifies the processing implementation.

M. Extension: Arbitrary Waveforms in Retrospective Acquisition

The disclosed algorithm enables high-precision (e.g., floating-point) transmit waveform synthesis in the retrospective TX-RX beamforming step, in contrast to the actual number of physical levels available in TX hardware such as a tri-state waveform pulser. This enables far higher achieved waveform fidelity in the acoustic medium compared to the discrete-level waveform synthesis technique.

Transmit pulses issued during retrospective transmission are limited in precision and bandwidth by the numeric precision of algorithmic processing and by simulation sample rate (effectively giving millions of available transmission levels with floating point processing. In contrast, voltage pulser designs and bandwidths in physical transmitter hardware typically allow only a few transmit levels, e.g., monopolar, bipolar, or tri-state. This retrospective transmission scheme permits high-fidelity arbitrary waveform synthesis for transducer frequency response compensation, temporal waveform design, and space-time wavefront design, by Step I of techniques described in the literature, the MMSE-based waveform computation, but not subject to limitations in Step II, the modulation symbol set selection and modulation for error minimization.

An example application benefitting from improved waveform fidelity is pulse-shape synthesis with compensation for transducer bandwidth roll-off. Below is an example using the retrospective compensating pulse design method. Here, an arbitrary-precision transmitter waveform is designed to generate a raised-cosine pulse at the face of the transducer, based on an empirically-determined impulse response of the transducer element. For comparison, the acoustic impulse response of the transducer is also shown in FIG. 16.

N. Extension: 2-D Probe/3-D Imaging with Reduced Transmit Events.

For 3-D applications using a 2-D array, the sparse transmit element acquisition scheme is generalized to two dimensions. Here, spherical waves, modulated by independent codes on each transmit channel, are generated from individual transmit elements, or from a region of elements referenced to a proxy virtual ("reference") element, the location of which is used in beamforming step, as illustrated in FIG. 17. In the case of spherical waves spatially originating from an array element, the reference element coincides with this origin. In the case of virtual apex transmission from each of the transmit sub-apertures, the origins of each spherical wave source is offset from the planar array, and its 3-D location information is used as the reference element in the beamforming step.

For lower spatial transmit power density, extended transmit elements are employed as they were in the case for 2-D imaging. In the extended element case, the beamforming step uses the center of the reference element to generate timing information.

The advantages of the technique include (1) improvement in contrast resolution and sensitivity compared to 3-D unfocused high-speed imaging techniques such as planewave imaging, where a lack of transducer elevational focus leads to more clutter than in a linear array with an elevation focus achieved by its lens; (2) improved depth of field and field of view compared to focused techniques; (3) improvement in framerate compared to focused techniques; (4) reduction of artifacts compared to other techniques that require zone blending, pixel-specific calibrated weightings, or other steps for de-mosaicing image appearance due to zone-based features of underlying processing.

O. Extension: Operator Optimization of Regularization Parameter by Interpretation as a Color Gain/Noise Threshold.

To optimize the regularization parameter needed in the under-determined IR models, or heterogeneous (mixed-effects) models applicable to restricted colorbox lag reconstruction, or limited/single-lag pixel-specific IR estimation models, the disclosed algorithm optionally present a control to the operator which effects a suitably ganged adjustment of relevant regularization parameters in the regularized model, or equivalently the relevant random effects variance parameters in the mixed effects model for combined tissue and flow medium impulse response estimation. The operator will then see the real-time, active adjustment of this parameter as controlling color sensitivity. In this usage, adjustment of the regularization parameter will correspondingly adjust a representative metric of expected flow signal power or variance in stochastically modeled impulse response lag parameters adjacent to those lags used for beamforming pixel of interest. Mis-adjustment of the parameter will appear as either excessive noise in color detection, or as a muting of color detections. Thus it will indicate a commensurate amount of correction required by the operator for the present image field to achieve the operator's intended sensitivity adjustment. In the extreme case of selecting vanishingly small flow power, the disclosed CER imaging algorithm will approach the matched-filter.

P. Extension: Coded Apertures.

A set of coded sequences is selected for simultaneous transmission. Each sequence drives a ganged set of transmit elements. The transmitting transducer element set is spatially modulated by applying numeric signs, (or otherwise code values) from the allowed spatial code set to specific transmit elements. For example, these codes could be comprised of elements from a Hadamard basis vector. Thus the specific temporal code sequence is applied for transmission through a subaperture that is in turn spatially modulated across the subaperture's component transmitter elements. Multiple, distinct transmit sequences are modulated likewise through the same set of transmitting elements in the subaperture, however with application of a distinct spatial code (for example, comprised of elements of a different Hadamard basis vector) selected distinctly for each transmit sequence. The set of transmit sequences formed by the resulting space-time modulations are summed together to get a single time waveform for each transmit element in the subaperture. The summed transmit sequence approximating the desired transmit waveforms can be applied through the transmitter hardware by employing the "DAC-synthesis" usage model. The subapertures with their multiple spatial codes then represent virtual transmit apertures and are included, according to their modulating temporal codes, in the impulse estimation model as described earlier in analogy to those of the physical aperture's impulse responses; although in this case the spatially coded apertures do not have a direct topological aperture interpretation. However, if the spatial transmit codes form a complete basis, then following impulse response estimation, the impulse response estimates are obtained for the individual transmit elements by applying the inverse transform of the spatial code set to the impulse responses in a subaperture.

Q. Extension: Transmission Nonlinearity Compensation.

Transmission nonlinearity is compensated by employing the transducer compensation usage model in the literature. Here, the parameters describing nonlinear dynamical components in the transmitter and transducer are identified. These parameters are used in model-based optimization of the transmit pulse sequence, employing dynamic programming or Viterbi algorithm techniques described in J. A. Flynn, "Method And System For Arbitrary Waveform Generation Using A Tri-State Transmit Pulser" U.S. Patent Application PCT/US2014/047080, Jul. 17, 2014, which is incorporated herein in its entirety. This optimized transmit pulse sequence compensates for the transmission nonlinearities to produce the desired acoustic waveform with a fidelity improved over that of conventional transmission. The fidelity optimization criterion may be restricted to frequencies within the transducer bandwidth, following the approach described in J. A. Flynn, "Method And System For Arbitrary Waveform Generation Using A Tri-State Transmit Pulser" U.S. Patent Application PCT/US2014/047080, Jul. 17, 2014. This improved fidelity enables improved performance of spectral Doppler, color flow imaging, and tissue motion imaging modes implemented with coded excitation transmit waveforms.

Adjunct to this technique, an enhancement is to restrict the desired transmit waveform, in a prior design step, to a limited bandwidth that would place harmonic and intermodulation distortion frequency components outside the transducer bandwidth. This is design can be accomplished, for example, by employing a raised-cosine band-limited prototype pulse [10] of the desired bandwidth, and modulating it with the desired transmit code.

R. Extension: Harmonic Imaging.

Using raised-cosine pulses [10] modulated with codes, band-limited waveforms are designed which have a time extent of many wavelengths. The band-limits are restricted to the lower portion of the transducer bandwidth. At sufficiently high transmit power levels, a second harmonic of the transmit signal is generated due to nonlinear propagation effects of the medium. Upon reception of the reflected acoustic signals, two filtered versions are created be restriction of appropriate frequencies. In addition to filtering, the two signal components are resampled as necessary. These versions of the signal represent the fundamental linear transmission and the nonlinear propagation components at a frequency spectrum that is commensurate with a doubling of the linear spectral region. The Impulse Response estimation model is extended by augmented measurements corresponding to the harmonic signal measurements. The resulting model thus generates two sets of impulse responses corresponding to the fundamental and harmonic impulse responses. Using the arbitrary waveform synthesis design techniques of J. Flynn, P. Kaczkowski, K. Linkhart, R. Daigle, "Arbitrary waveforms using a tri-state transmit pulser," in *Ultrasonics Symposium (IUS)*, 2013 *IEEE International*, Prague, Czech Republic, July 2013, pp. 41, 44, 21-25 and J. A. Flynn, "Method And System For Arbitrary Waveform Generation Using A Tri-State Transmit Pulser" U.S. Patent Application PCT/US2014/047080, Jul. 17, 2014, the desired transmit waveform, with its specific bandlimited properties, is coded into the transmitter voltage levels. The coding and SNR gains provided by the disclosed CER algorithm provide enhanced detection of the harmonic propagation signal components.

S. Extension: Extended Spectrum Imaging.

Transmission at the transducer's extreme upper band edge with compensated pulses is achieved by employing the transducer compensation usage model in J. Flynn, P. Kaczkowski, K. Linkhart, R. Daigle, "Arbitrary waveforms using a tri-state transmit pulser," in *Ultrasonics Symposium (IUS)*, 2013 *IEEE International*, Prague, Czech Republic, July 2013, pp. 41, 44, 21-25 and J. A. Flynn, "Method And System For Arbitrary Waveform Generation Using A Tri-State Transmit Pulser" U.S. Patent Application PCT/US2014/047080, Jul. 17, 2014. Compensation for expected frequency-dependent attenuation is incorporating into the transmitted waveform design. Because of coding gain achievable with coded excitation, attenuation that accompanies higher transmit frequencies is mitigated.

T. Extension: Current-Sense Empirical Transmit Model.

To more accurately construct convolutions models of Section II.B, II.C, and II.H, the transmitter current may be estimated by measuring voltage across a resistive element in series with the pulser voltage or current source. The current measurement waveform can be used as an estimate of the implied voltage across the transducer element during transmit. In turn the transmit element voltage can be used as a proxy for transmitted symbol values in the impulse response estimation models. In this manner, errors and/or noise in the transmitted pulse sequences are suppressed in the impulse response estimates, and thus can be mitigated in the case of Doppler or shear wave imaging.

FIG. 18 shows the CER algorithm in a B-mode application with Philips L7-4 transducer, applied in vivo to image a carotid artery. The example uses a sparse transmit aperture of 26 elements, with 48 acquisition events each transmitting a unique set of codes. Transmitted codes have 24 symbols each.

U. Extension: Inverse Scattering from Impulse Response Estimates.

The coded excitation impulse response method applies as well to retrospective reconstruction that is not conventional beamforming, but rather inverse scattering. In this case of inverse scattering as the retrospective reconstruction method, the entire set of pixels $F_{IS}$, representing target image reflectivity defined on an image grid (and collapsed lexicographically into vector format), is mapped to the complete transmit-receive impulse response estimate set H of Equation (1-19) by $$H=GF_{IS}$$

according to the loci of equidistant round-trip propagation times as shown in FIG. 8. Here, in analogy to the selection and interpolation executed by rows of matrices B and A in Equation (1-19), the rows of matrix Gamma select scattering reflectivity values in a locus equidistant from a transmit-receive pair, according to the corresponding lag index of the row of interest of the column vector H.

The large system is very sparse and can be solved for the unknown image pixels FIS by iterative solver techniques such as LSQR in combination with appropriate preconditioners, and with initial values set by SAIF retrospectively beamformed images from the current or previous frame. This technique is explored for non-imaging communications arrays in Flynn, J. A.; Ritcey, J. A., "Turbo array receiver for underwater telemetry," *Signals, Systems and Computers, 2004. Conference Record of the Thirty-Eighth Asilomar Conference on*, Vol. 2, 7-10 Nov. 2004, pp. 1421,1425 and J. A. Flynn, "Computation and Architectures for Array Receivers in Large Delay-Doppler Spreading," Ph.D. dissertation, Dept. Elect. Eng., Univ. of Washington, Seattle, Wash., 2004.

In contrast to inverse scattering models based on predicted pixel-specific point spread function, or based on pixel-specific predicted field values, the impulse response model generalizes well for actual (observed) scattering that falls spatially between design grid pixel locations. This eases the task of regularization methods employed in the inversion step. The benefit of this method is improved image point-spread-function figures of merit.

V. Extension: Coded Planewaves and Doppler Processing.

Planewave Doppler processing is improved in sensitivity by applying the proposed algorithm with special code constraints and processing. In this scheme, the excitation code is common across all transducer elements in the transmit aperture, excepting steering delays that specify the propagation direction of the PW. A pair of distinct codes [c1, c2], each of length $N_C$, is used for every successive pair of acquisition cycles (PRIs), so that the transmitted code sequence is [c1,c2,c1,c2, . . . ,c1,c2] for an even number K of acquisitions. The pairs of acquisitions are then processed for MISO IR estimation per the algorithm of Section II.B, treating the transmit aperture as a single, wide, transmit element, generating a length—K/2 sequence of IR estimate sets for the case of M=1. From this IR estimation set, subsequent retrospective acquisition and beamforming is executed per Section II.D, subject to incorporation of delays appropriate for PW transmission and receive beamforming. By this approach, any systematic clutter introduced by transmitter non-idealities is stationary in Doppler slow-time, and can be removed by conventional Doppler processing on the resultant K/2 images. While the penalty with this method is the 2:1 reduction of the Nyquist maximum Doppler frequency, the benefits compare to conventional PW are (1) increased sensitivity for a given transmit voltage and ensemble length, due to the plurality of symbol cycles in the transmitted codes, and (2) reduction of reconstruction clutter from temporal post-peak trailing artifacts in the PW approximation transmit, due to the spatially sampled nature of the discrete-element array. This reduction is enabled by the fact that each modeled IR lag (time) is comprised of scattering from a locus of points in the media, each of which is ensonified by a different pattern of trailing artifacts in the transmitted PW; in the aggregate, the patterns thus do not sum coherently over the locus, nor do they fit the convolution model common across the locus, and so are suppressed.

This algorithm variant enables high-framerate, multi-point, quantitative spectral Doppler with more effective clutter, sidelobe, and sensitivity performance compared to other techniques.

W. Extension: Non-Uniform Pulse Stacking Model for High-Doppler or High Frame-Rate Imaging.

The impulse response model variant denoted "Pulse Stacking" in Section II.H "Impulse Response Model Variants" and Section III.F "Ultra-High Doppler Signal Estimation" is generalized here to the case of irregular or non-uniform transmit burst intervals, for the purpose of mitigating artifacts such as target ghosting, spurious target replicas, or regions of high noise in image or impulse response estimates, due to necessary receiver blanking periods.

In conventional pulse stacking approaches, designed to extend alias-free estimation of Doppler frequencies higher than the Doppler Nyquist rate, multiple spurious returns from targets can appear in reconstructed images because the medium is interrogated at an acquisition rate higher than permitted by the acoustic round-trip time. This penalty for achieving measurements of Doppler, in a conventional approach, requires careful selection of imaging windows to avoid spectral replicas. In the pulse-stacking model design disclosed in Section II.H, ghosting is mitigated, however bands of high estimation noise regions appear due to receive blanking. The blanking regions occur in the RF data measurement whenever a transmit event is present.

The blanking process is to censor (by deletion) the coincident samples from the RF data measurement vector (e.g., in FIG. 7 "Schematic of sparsity structure for high-Doppler model (two acquisition intervals)"). Corresponding rows of the model matrix are also censored by deletion. This process produces the "pointed" non-zero model structure regions seen in FIG. 7. When these "pointed" regions are aligned vertically at a given column in the matrix, the precision of the resulting estimates for the model degrades significantly for estimands in corresponding rows of the impulse response vector. This effect is readily predicted by the inverse Grammian of the model matrix, per standard Linear Model Theory [8]. In the non-uniform pulse stacking method proposed here, the transmit interval times are modulated non-uniformly, so that the concept of a constant PRF is violated. The benefit of this is a dithering in the blanking intervals, resulting in misalignment of the pointed regions in the model matrix. This effect greatly improves the precision to a relatively uniform value across the impulse response vector elements.

To demonstrate this effect, the relative precision is compared for a hypothetical uniform pulse stacking arrangement, and a non-uniform pulse stacking model. In this example, the uniform model has a super-high PRF that is three-fold the acoustic round trip time limit. The hypothetical non-uniform model, in this case having random transmission times, has a much higher average inter-transmission rate, which is approximately nine-fold the acoustic limit. The two models are normalized for equivalence in transmit power. The result is seen in the precision plots of FIG. 19. Here it is apparent that the uniform stacking model shows regions of high noise at lag indices associated with the receiver blanking periods, while the non-uniform transmission pulse stacking model has an even distribution of impulse response estimation variance, and has no significant artifacts of noise bands.

A portion of the non-uniform pulse-stacking model used in the example is shown in FIG. 20. On the left panel, the model matrix is shown prior to receiver blanking. On the right panel, the blanking regions have been censored by deletion. It is apparent from the image that the pointed regions in the model are misaligned vertically throughout the non-uniform model. This gives a heuristic view of how the nonuniform transmission intervals mitigate noise bands due to receiver blanking.

In the extension of the model to stationary tissue rejection (STR) and Fourier processing discussed in Sections II.I, III.C and III.D, for flow or tissue motion estimation, the corresponding augmented models terms for polynomial or Fourier basis vectors must be sampled on the nonuniform times corresponding to the pulse transmissions. One approximation is to assume these times are piecewise constant, so that for a given transmitted burst, the basis functions are also constant during the burst. However, this is readily generalized to exact time support for the basis functions, if for example extremely long bursts are employed.

Implementations

The forgoing disclosure can be implemented as described in the representative examples below, which are provided as a non-inclusive, non-limiting set of examples.

The that implements a two-step method for coded excitation imaging first estimates the medium's impulse response (IR), then by retrospective transmission through the IR set, synthesizes virtual wavefronts for beamforming. In step one, coded waveforms are transmitted simultaneously on multiple elements for several frames. A multi-input, single output (MISO) system is constructed from the codes to model transmit-receive paths. The system and RF data observation are solved by linear model theory, giving an IR set for the medium. In step 2, the estimates are subsequently applied to a secondary MISO system, constructed by analogy to the first, but with pulses convenient for beamforming, e.g., a focused set of single-cycle pulses for ideal focused reconstruction. Thus, the probing sequence can be optimally designed for IR characterization under acoustic time budget, while the retrospective acquisitions are synthesized outside of acoustic time.

The method of ultrasonic imaging is implemented in one form that includes the following steps, substantially in the order provided: transmitting coded waveforms simultaneously on multiple elements for several frames; constructing a first multi-input, single output (MISO) system from the codes to model transmit-receive paths; solving system and RF data observation by linear model theory, giving an IR set for the medium; and applying the estimates to a secondary MISO system, constructed by analogy to the first, but with pulses configured for beamforming in the form of a focused set of single-cycle pulses for focused reconstruction.

The foregoing method of ultrasonic imaging can be modified so that the steps are substantially in the order as follows: using coded excitation transmission emitted from multiple transducer elements or apertures simultaneously over a time sequence of multiple acquisition events, processing subsequently received RF ultrasound data on transducer elements in a manner that estimates a set of multi-input-single-output (MISO) impulse response acoustic models, one for each transmit-receive transducer channel pair; and subsequently employing a secondary step comprising virtual acquisition of virtual RF data through excitation of the MISO model repeatedly as a proxy for the imaged media present, and subsequently beamforming or image reconstruction using the virtual RF data to produce imagery.

An alternative form of a method of ultrasonic imaging using the description herein includes emitting acoustic signals into a medium simultaneously from multiple transducer elements using coded excitation transmission over a time sequence; receiving echo signals at the multiple transducer elements in response to the emitting; processing the received echo signals in a manner that estimates a set of multi-input-single-output (MISO) impulse response acoustic models, one for each transmit-receive pair at each transducer element; acquiring virtual data through excitation of the MISO model repeatedly as a proxy for the imaged media present, and image reconstruction using the virtual data to produce a visual image on a display device.

A method for ultrasonic tissue motion imaging may also be implemented in the following steps substantially in the order listed: emitting acoustic signals into a medium simultaneously from multiple transducer elements using coded excitation transmission over a time sequence; receiving echo signals at the multiple transducer elements in response to the emitting; processing the received echo signals, which comprises estimating a set of multi-input, single-output (MISO) impulse response acoustic models, one for each transmit-receive pair at each transducer element and that retains corresponding estimation fitting error residuals conforming to data used, so that stationary tissue signals are rejected in the fitted residuals, while blood flow or motion-induced Doppler signals of interest are retained therein; and processing the residuals data to produce blood flow or moving tissue imagery.

A system implementation of the forgoing methods would utilize the following components: means for transmitting coded waveforms simultaneously on multiple elements for several frames; means for constructing a first multi-input, single output (MISO) system from the codes to model transmit-receive paths; means for solving system and RF data observation by linear model theory, giving an IR set for the medium; and means for applying the estimates to a secondary MISO system, constructed by analogy to the first, but with pulses configured for beamforming in the form of a focused set of single-cycle pulses for focused reconstruction. Such means are described herein or are well known to those skilled in the art.

Additional implementations of the foregoing methods are described below with variations and preferences in the form of non-limiting examples.

Example (1)

A method of ultrasonic imaging by coded excitation reconstruction (CER) that includes using coded excitation transmission emitted from multiple transducer elements or apertures simultaneously over a time sequence of multiple acquisition events, processing subsequently received RF ultrasound data on transducer elements in a manner that estimates a set of multi-input-single-output (MISO) impulse response acoustic models, one for each transmit-receive transducer channel pair; and subsequently employing a secondary step comprising virtual acquisition of virtual RF data through excitation of the MISO models repeatedly as a proxy for the imaged media present, and subsequently beamforming or image reconstruction using the virtual RF data to produce imagery.

Example 1.1

The foregoing method of Example (1), modified by insuring the disclosed imaging method incurs minimal mechanical index, or best margin against transmit element destructive voltage limit, or other per-element transmit voltage limits based on hardware limitations or subject safety, employs transmit codes that are time-space diverse and simultaneous across multiple transmitting transducer elements (or collections of elements effecting multiple apertures), for several transmit-receive acquisition events, generating non-coherent or incoherent physical acoustic fields, which are transformed by appropriate processing of the known transmit codes. This transformation produces a set of acoustic scattering models that are subsequently processed with virtual acquisition and beamforming or reconstruction by virtual transmissions which can be focused or unfocused, or of coherent or noncoherent nature.

Example (1.2)

The method of Example (1), where coded excitation waveforms are transmitted and processed to produce best linear unbiased (BLUE) impulse response estimates, or impulse response estimates of otherwise controlled accuracy and precision, and consequently the MISO acoustic model enjoying those optimality properties; and where subsequent virtual acquisition and beamforming employing the model enables retrospective estimation of Synthetic Aperture Ideal Focus (SAIF) imagery, or any other retrospective imaging or signal estimation that uses a subset of the physical transmit apertures subject to their bandwidth and linearity and motion assumptions of the interrogated medium, that is best linear and unbiased (BLUE), or of optimally controlled accuracy and precision.

Example (1.3)

The method of Example (1), of producing beam-steered or phased-array imaging with lambda-spaced transducer arrays and consequent proportionally-improved lateral resolution, while suppressing grating lobe artifacts; wherein the disclosed imaging method allows effective transducer bandwidth compensation due to high SNR of the coded excitation processing; in which the bandwidth compensation permits effective wideband imaging with lambda-spaced transducer arrays while suppressing grating lobes.

Example (1.4)

The method of Example (1), where ultrasonic imaging of moving tissue is accomplished by CER executed in a sliding-window reconstruction (SWR) fashion, thereby processing sequential, overlapping, contiguous temporal subsets of space-time diverse transmitted codes corresponding to commensurate subsets of acquisition events, so that each processing interval generates a CER-derived image corresponding to codes transmitted in the subset interval, thereby producing an image sequence representative of motion present during the entire acquisition sequence, suitable for shear wave detection imaging.

Example (1.4.1.1)

The method of Example (1.4)), where SWR-CER processing produces an image sequence representative of motion present during the entire acquisition sequence; upon which further pixel-wise processing is executed to accomplish wall-motion or stationary tissue signal rejection and subsequent Doppler frequency estimation, effecting Doppler flow imaging or spectral Doppler analysis.

Example (1.4.1.2)

The method of Example (1.4)), where SWR-CER processing produces an image sequence representative of motion present during the entire acquisition sequence; upon which further pixel-wise processing is executed to accomplish subsequent Doppler frequency estimation, effecting Doppler tissue motion imaging.

Example (1.4.1.3)

The method of Example (1.4)), where SWR-CER processing produces an image sequence representative of motion present during the entire acquisition sequence; upon which further pixel-wise processing is executed to accomplish subsequent shear-wave detection, effecting shear-wave imaging.

Example (1.5)

The method of Example (1), wherein polynomial, Fourier, or other low-rank models of impulse response lag time evolution provide fidelity to the estimation of signal components due to moving tissue or scattering, and thereby provide commensurate robustness in rejection of motion artifacts from the B-Mode imagery.

Example (1.6)

The method of Example (1), wherein the retrospective acquisition events applied to the estimated MISO acoustic model employ retrospective (virtual) transmit waveforms defined uniquely for virtual transmit channel and uniquely for each pixel to be imaged, so that an optimal tradeoff in sensitivity, spatial resolution, and contrast resolution is achieved for each pixel in the image.

Example (1.7)

The method of Example (1), wherein physical transmission of a plurality of distinct codes simultaneously over a set of transducer elements is generalized to transmit on ganged distinct subsets of transducer elements, each subset forming a subarray or subaperture the elements of which are excited identically, or excited identically other than element-specific delays effecting steering or focusing at a spatial point.

Example (1.8)

The method of Example (1), wherein physical transmission of a plurality of distinct codes simultaneously over a set of transducer elements is generalized to transmit over a set of co-located apertures, each employing all available transducer array elements, and each defined by focusing delays effecting desired physical focus locations, so that multiple simultaneous wavefronts modulated by distinct temporal codes are generated, each using all available transmitter elements; and wherein the modulating array signals effecting the resulting acoustic array transmissions are sums of the individual array signals of the individual aperture coded modulations in the case of linear continuous level transmit amplifiers, or discrete-state encodings of the array signal summations in the case of discrete-level amplifiers.

Example (1.9)

The method of Example (1), wherein the retrospective acquisition events applied to the estimated MISO acoustic model employ arbitrary retrospective (virtual) transmit waveforms defined at the precision of available computation resources, so that effective imaging waveform fidelity is not limited by transmitter precision of the physical hardware; thereby enabling imaging with enhanced transducer bandwidth and commensurate axial resolution improvement of imaging.

Example (1.10)

The method of Example (1), where the impulse response estimation step employs transmit codes that are time-space diverse and simultaneous across multiple transmitting transducer elements (or collections of elements effecting multiple apertures), for several transmit-receive acquisition events, which are transformed by appropriate processing of measurements of the constituent transmissions corrupted nonlinearly and possibly with time-varying transformation by transmitter hardware non-idealities; where the measurements are conducted so as to constitute a proxy of the achieved transmit voltage waveforms due to transmitted symbol values; and where the transformation produces a set of acoustic scattering models that are subsequently processed with virtual acquisition and beamforming or reconstruction by virtual transmissions to effect imaging.

Example (1.11)

The method of Example (1), wherein enhanced resolution of extended-spectrum imaging is effected by transmission at the transducer's extreme upper band edge, enabled by compensation for expected frequency-dependent attenuation of the transducer elements through transmitted waveform design; and wherein because of coding gain achievable with the underlying coded excitation transmission, attenuation that accompanies higher transmit frequencies is mitigated.

Example (1.12)

The method of Example (1), wherein enhanced harmonic imaging is effected by transmission of coded excitation sequences modulating bandlimited pulses, where the pulses are designed with spectral vacancy in the harmonic band, so that harmonics generation at transmit is mitigated; thereby allowing more accurately received harmonics due to nonlinearities in the imaged media.

Example (1.13)

The method of Example (1), of producing ultrasonic imagery with mitigation of ghosting and other artifacts, at frame-rates beyond those commensurate with the acoustic round trip limit of the employed imaging window depth; and of generating ultrasonic imagery over imaging window depth spans greater than those commensurate with the employed contiguous receiver interval; and of generating ultrasonic Doppler imagery or estimates, with mitigation of frequency aliasing, over Doppler frequencies greater than those commensurate with the acoustic round trip limit of the employed imaging window or Doppler measurement window depth; comprising employing transmit-receive intervals substantially less than the length of the acoustic impulse response of the imaged media interrogated by the transducer array elements; and using transmit-receive intervals scheduled at times dithered randomly or irregularly; and aggregating array RF measurements of the dithered transmit-receive intervals in a manner in consideration of multiple overlapping impulse responses for an accurate MISO model explaining the observed measurements.

Example (1.13.1)

The method of Example (1.13), of mitigating deleterious effects of transmitter nonlinearities to Doppler processing, comprising employing successive frames of transmit-receive scheduling having identical transmit-receive schedule dithering and identical excitation code sequence realizations.

Example (1.14)

The method of Example (1), of producing 3-dimensional imagery from 2-dimensional transducer arrays, with the qualities of having high frame-rate; high SNR and sensitivity, low mechanical index and spatial power density, suppressed mosaicing and zone blending artifacts; comprising, for the coded excitation transmission step, the selection of a suitably distributed subset of transducer array elements as transmit apertures, or as reference elements in the case of extended transmit subapertures; and transmitting spherical, or unfocused waves of origin at the transmit element or at a virtual apex offset from the array; and in the retrospective acquisition and beamforming step, using the locations of the transmit aperture set or reference element or virtual apex as applicable, to define beamforming delays and effect imaging.

Example (1.15)

The method of Example (1), wherein physical transmission of a plurality of distinct codes simultaneously over a set of transducer elements is generalized to transmit over a set of co-located apertures, each aperture employing all available transducer array elements, and each aperture defined by a secondary coding that is spatial across the aperture, so that multiple simultaneous aperture-coded wavefronts each modulated by distinct temporal codes are generated, each using all available transmitter elements; and wherein the modulating array signals effecting the resulting acoustic array transmissions are sums of the individual array signals of the individual aperture coded modulations in the case of linear continuous level transmit amplifiers, or discrete-state encodings of the array signal summations in the case of discrete-level amplifiers.

Example (1.16)

The method of Example (1), where fidelity of the desired coded modulation signal transmission is preserved in the presence of transmitter and transducer nonlinearities, comprising precompensation of the transmit signal, the precompensation being determined by optimization of a fidelity criterion constrained by a model incorporating identified nonlinearity parameters, so that the desired acoustic waveform is produced with a fidelity improved over that of an uncompensated transmission.

Primary Example (2)

A method of ultrasonic blood flow or tissue motion imaging or estimation, comprising using coded excitation transmission emitted from multiple transducer elements or apertures simultaneously, processing subsequently received RF ultrasound data on transducer elements in a manner that estimates a set of multi-input, single-output (MISO) impulse response acoustic models, one for each transmit-receive transducer channel pair; and that retains corresponding estimation fitting error RF residuals conforming to the RF data used, so that stationary tissue signals are rejected or suppressed in the RF fitted residuals, while blood flow or motion-induced Doppler signals of interest are retained therein; and subsequently employing a furthers steps comprising processing the RF residuals data to produce blood flow or moving tissue imagery or estimates.

Example (2.1)

The method of Example (Doppler), wherein polynomial, Fourier, or other low-rank basis time-varying convolution models for impulse response lag-time evolution provide fidelity to the estimation of signal components due to stationary or slowly moving tissue or scattering, and thereby providing commensurate robustness in separation and rejection of unwanted tissue motion signal components from the desired Doppler signal retained in the RF fitted residuals.

Example (2.2)

The method of Example (2.1), where Doppler imagery or estimates are provided by subsequent processing of the RF fitted residual data, comprised of secondary CER processing that employs a Fourier basis or partial Fourier basis for time-varying convolution models of impulse response lag-time evolution; the impulse response sets generated therein forming a spectrum of MISO models of transmit-receiver channel pairs, one for each employed Fourier coefficient; and retrospective virtual acquisition and beamforming on each Fourier-coefficient MISO estimate set thereof, forming a spectrum of images each corresponding to Fourier estimates of Doppler frequencies employed; on which data color flow Doppler detection and display functions, or spectral Doppler presentation modes are applied.

Example (2.2.1)

The method of Example (2.2), where vector flow or motion imagery or estimates are provided by subsequent processing of the RF fitted residual data, comprised of secondary CER processing that employs a Fourier basis or partial Fourier basis for time-varying convolution models of impulse response lag-time evolution; the impulse response sets generated therein forming a spectrum of MISO models of transmit-receiver channel pairs, one for each employed Fourier coefficient; selection of a two-dimensional sampling grid of a vector motion velocity estimate range of interest; retrospective virtual acquisition and subsequent beamforming of each image reconstruction pixel employing for each constituent transmit-receive channel pair the Fourier-coefficient MISO estimates interpolated to the Doppler frequency determined by the bistatic range-rate equation value for the pixel and vector velocity grid point, therein producing a spectrum of images each corresponding to the vector velocity grid points of interest.

Example (2.3)

The method of Example (2.1), where Doppler imagery or estimates are provided by subsequent processing of the RF fitted residual data, comprised of employing pulse-compression matched filters corresponding to expected acoustic signatures at each imaged pixel location, followed by receive beamforming producing an image for each acquisition event or pulse repetition interval (PRI); on which data Doppler processing is applied pixel-wise and over PRI index to produce color flow Doppler images or Doppler spectral modality estimates.

Example (2.4)

The method of Example (2.1), where Doppler imagery or estimates are provided by subsequent processing of the RF fitted residual data, comprised of secondary CER processing that employs a Fourier basis or partial Fourier basis for time-varying convolution models of impulse response lag-time evolution; the impulse response sets generated therein forming a spectrum of MISO models of transmit-receiver channel pairs, one for each employed Fourier coefficient; over which each impulse response lag value is processed over its spectrum of Fourier frequency indices by inverse Fourier transform to generate a time history for each lag value, producing a time history of MISO models; and retrospective virtual acquisition and beamforming of the MISO estimate set thereof, forming a time history of images each corresponding to an acquisition event time; on which data set color flow Doppler processing or spectral Doppler processing is applied to enable respective Doppler modality.

Example (2.5)

The method of Example (2.1), where Doppler imagery or estimates are provided by subsequent processing of the RF fitted residual data, comprised of secondary CER processing that employs pixel-specific, heterogenous (or mixed-effects) partitioning of its MISO model into a subset of lags needed for reconstructing the pixel of interest (POI), and the remainder of lags contributing reflected signal from other pixels to the RF measurement; wherein the MISO model has stochastic specification for lag parameters that reflects low variance or deterministic nature to the POI-associated lag partition, while the remainder are modeled stochastically with higher variance to accomplish regularization of the model; the impulse response sets generated therein forming a time-sequence of MISO models of transmit-receiver channel pairs, solved independently for each acquisition event or pulse repetition interval (PRI), providing a MISO model estimate of flow scattering for each PRI; followed by retrospective virtual acquisition and beamforming on each acquisition MISO estimate thereof, forming a time-sequence of images each corresponding to a PRI; on which data color flow Doppler or spectral Doppler processing is executed pixel-wise and over all PRI times, thereby providing Doppler flow imagery or spectral Doppler modality estimates.

Example (2.5.1)

The method of Example 2.5, further including the effective setting of values of regularization parameters or stochastic flow signal description parameters, suitably ganged to allow interactive adjustment by human operator, or by clinical optimizing procedure or automated agent, to effect a detection gain threshold for qualifying pixels in color flow Doppler imagery.

Primary Example (3)

A method of ultrasonic imaging by coded excitation reconstruction (CER) to include using coded excitation transmission emitted from multiple transducer elements or apertures simultaneously over a time sequence of multiple acquisition events, processing subsequently received RF ultrasound data on transducer elements in a manner that estimates a set of multi-input-single-output (MISO) impulse response acoustic models, one for each transmit-receive transducer channel pair; and subsequently employing a secondary step comprising mapping the desired image pixel grid of scattering reflectivity to a predicted impulse response set corresponding to scattering loci of equidistant round-trip propagation (ERTP) times for the employed set of transmit-receive element pairs; forming a model with the described ERTP mapping; employing the impulse responses estimated in the first IR estimation step as measurements due to the predicted ERTP impulse response model operating on unknown hypothetical scattering grid; and solving for the unknown hypothetical scattering in the resulting linear equation system to effect imaging.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of ultrasonic imaging by coded excitation reconstruction (CER), comprising:
emitting an ensemble of acoustic signals at a pulse repetition frequency into a medium from multiple transducer elements in a transducer using coded excitation transmission of binary symbols employed in a phase-shift keying (BPSK) modulation of a one-cycle waveform configured for the multiple transducer elements;
receiving echo signals at the multiple transducer elements in response to the emitting;
processing the received echo signals to estimate a medium impulse response between every transmit element and every receive element of the multiple transducer elements using a set of multi-input-single-output (MISO) models in accordance with statistical linear model theory;
acquiring virtual receive data through simulated transmit excitation of the MISO models repeatedly as a proxy for imaging of the medium; and
performing image reconstruction using the virtual data to produce a visual image on a display device.

2. The method of claim 1, wherein the emitting comprises emitting the acoustic signals using coded excitation transmission waveforms to produce best linear unbiased (BLUE) impulse response estimates; and wherein the acquiring virtual data and image reconstruction steps employing the MISO models enables estimation of retrospective imaging or signal estimation that uses a subset of the physical transducer elements that is best linear and unbiased (BLUE).

3. The method of claim 1, wherein the multiple transducer elements comprise lambda-spaced transducer arrays and wherein the emitting comprises producing beam-steered or phased-array imaging with the lambda-spaced transducer arrays to obtain proportionally-improved lateral resolution, while suppressing grating lobe artifacts.

4. The method of claim 1, where the emitting the impulse response includes utilizing coded excitation transmission codes that are time-space diverse and simultaneous across multiple transducer elements for several transmit-receive acquisition events, which are transformed by processing of measurements of transmissions corrupted nonlinearly or with time-varying transformation; where the measurements are conducted so as to constitute transmit voltage waveforms due to transmitted symbol values, and where the time-varying transformation produces a set of acoustic scattering models that are subsequently processed with virtual acquisition and beamforming to effect imaging on the display device.

5. A method of ultrasonic tissue motion imaging, comprising:
emitting acoustic signals into a medium simultaneously from multiple transducer elements using primary coded excitation transmission over a time sequence;
receiving echo signals at the multiple transducer elements in response to the emitting;
processing the received echo signals, which comprises estimating a set of multi-input, single-output (MISO) impulse response acoustic models, one for each transmit-receive pair at each transducer element, and that retains corresponding estimation fitting error residuals conforming to data used, so that stationary tissue signals are rejected in the estimation fitting error residuals, while blood flow or motion-induced Doppler signals are retained therein;
processing the estimation fitting error residuals data to produce blood flow or moving tissue imagery; and
subsequent processing of the estimation fitting error residuals data to provide at least one of vector flow, motion imagery, and motion estimates, the subsequent processing comprising secondary coded excitation transmission processing that employs a Fourier basis or partial Fourier basis for time-varying convolution models of impulse response lag-time evolution to generate impulse response sets that form a spectrum of MISO models of transmit-receiver transducer element pairs, one for each employed Fourier coefficient; selecting a two-dimensional sampling grid of a vector motion velocity estimate range of interest; retrospective virtual acquisition and subsequent beamforming of each image reconstruction pixel employing for each constituent transmit-receive transducer element pair of the Fourier-coefficient MISO models interpolated to the Doppler frequency determined by the bistatic range-rate equation value for the pixel and vector velocity grid point, therein producing a spectrum of images each corresponding to the vector velocity grid points of interest.

6. A method of ultrasonic tissue motion imaging, comprising:

emitting acoustic signals into a medium simultaneously from multiple transducer elements using primary coded excitation transmission over a time sequence;

receiving echo signals at the multiple transducer elements in response to the emitting;

processing the received echo signals, which comprises estimating a set of multi-input, single-output (MISO) impulse response acoustic models, one for each transmit-receive pair at each transducer element, and that retains corresponding estimation fitting error residuals conforming to data used, so that stationary tissue signals are rejected in the estimation fitting error residuals, while blood flow or motion-induced Doppler signals are retained therein;

processing the estimation fitting error residuals data to produce blood flow or moving tissue imagery; and subsequent processing of the estimation fitting error residuals data by secondary coded excitation transmission processing that employs a Fourier basis or partial Fourier basis for time-varying convolution models of impulse response lag-time evolution to generate impulse response sets that form a spectrum of MISO models of transmit-receiver transducer element pairs, one for each employed Fourier coefficient; over which each impulse response lag value is processed over its spectrum of Fourier frequency indices by inverse Fourier transform to generate a time history for each lag value and producing a time history of MISO models; and retrospective virtual acquisition and beamforming of the MISO estimate set thereof to form a time history of images each corresponding to an acquisition event time; and applying at least one of a color flow Doppler processing and spectral Doppler processing to enable respective Doppler modality.

7. The method of claim 6 wherein Doppler imagery or Doppler spectral modality estimates are provided by subsequent processing of the estimation fitting error residuals data by secondary coded excitation transmission processing that employs pixel-specific, heterogeneous partitioning of its MISO model into a subset of lags configured for reconstructing the pixel of interest (POI), and the remainder of lags contributing reflected signal from other pixels to an RF measurement; wherein the MISO model has a stochastic specification for lag parameters that reflects a first variance or deterministic nature to the POI-associated lag partition, while the remainder are modeled stochastically with a second variance that is higher than the first variance to accomplish regularization of the model to thereby generate impulse response sets that form a time-sequence of MISO models of transmit-receiver channel pairs, solved independently for each pulse repetition interval (PM), providing a MISO model estimate of flow scattering for each PM; followed by retrospective virtual acquisition and beamforming on each acquisition MISO estimate thereof to form a time-sequence of images that correspond to a PM; and applying at least one of data color flow Doppler processing and spectral Doppler processing executed pixel-wise and over all PM times to provide at least one of Doppler flow imagery and spectral Doppler modality estimates.

* * * * *